(12) United States Patent
Haynes et al.

(10) Patent No.: US 11,191,642 B2
(45) Date of Patent: Dec. 7, 2021

(54) CARDIAC VALVE LOADING DEVICES AND SYSTEMS

(71) Applicant: Cephea Valve Technologies, Inc., San Jose, CA (US)

(72) Inventors: Evelyn Haynes, Soquel, CA (US); Diana Chu, Ithaca, NY (US); Peter Gregg, Santa Cruz, CA (US); Randolf Von Oepen, Aptos, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 86 days.

(21) Appl. No.: 16/661,441

(22) Filed: Oct. 23, 2019

(65) Prior Publication Data

US 2020/0129292 A1    Apr. 30, 2020

Related U.S. Application Data

(60) Provisional application No. 62/750,731, filed on Oct. 25, 2018.

(51) Int. Cl.
*A61F 2/24*     (2006.01)
*A61F 2/95*     (2013.01)
*A61F 2/966*    (2013.01)

(52) U.S. Cl.
CPC .......... *A61F 2/2436* (2013.01); *A61F 2/9525* (2020.05); *A61F 2/9517* (2020.05); *A61F 2/9522* (2020.05); *A61F 2002/9665* (2013.01)

(58) Field of Classification Search
CPC .... A61F 2/2436; A61F 2/9525; A61F 2/9522; A61F 2/9517; A61F 2002/9665;
(Continued)

(56) References Cited

U.S. PATENT DOCUMENTS

2002/0183827 A1* 12/2002 Derus ................... A61F 2/9525
                                                   623/1.12
2014/0276408 A1*  9/2014 Abbate ................. A61M 29/00
                                                    604/106
(Continued)

FOREIGN PATENT DOCUMENTS

EP            2638884 A1     9/2013

OTHER PUBLICATIONS

Partial International Search Report for Application No. PCT/US2019/057675 dated Feb. 5, 2020, 8 pages.

*Primary Examiner* — Melanie R Tyson
*Assistant Examiner* — Andrew P. Restaino
(74) *Attorney, Agent, or Firm* — Lerner, David, Littenberg, Krumholz & Mentlik, LLP

(57) ABSTRACT

A loading device configured to radially collapse an expandable medical implant may include an operating handle having an opening therein extending along a longitudinal axis, a native sheath coupled to the operating handle and partially extending into the opening, such that the native sheath is configured to translate relative to the operating handle parallel to the longitudinal axis, a removable sheath removably coupled to the native sheath, an actuation rod extending parallel to the longitudinal axis at least partially through the opening, a lumen of the native sheath, and a lumen of the removable sheath, a distal end of the actuation rod being configured to be removably coupled to the expandable medical implant, and a first control element movable relative to the operating handle and coupled to the native sheath, the first control element being configured to translate the native sheath and the removable sheath relative to the operating handle.

6 Claims, 25 Drawing Sheets

(58) Field of Classification Search
CPC .......... A61F 2/24; A61F 2/2427; A61F 9/007; A61F 2/9526; A61F 2/952; A61F 2/95; A61F 2/011; A61B 17/2841; A61B 2017/0046; A61B 2017/2918; A61B 2017/305

See application file for complete search history.

(56) References Cited

U.S. PATENT DOCUMENTS

| | | | |
|---|---|---|---|
| 2014/0296905 A1* | 10/2014 | Dela ................. | A61B 17/50 606/200 |
| 2016/0135972 A1* | 5/2016 | Vad ................. | A61F 2/9661 606/108 |
| 2018/0014925 A1 | 1/2018 | Giordano et al. | |
| 2018/0028314 A1 | 2/2018 | Ekvall et al. | |
| 2018/0092744 A1 | 4/2018 | von Oepen et al. | |
| 2018/0280174 A1* | 10/2018 | Dwork ................. | A61F 2/2436 |
| 2018/0344456 A1* | 12/2018 | Barash ................. | A61F 2/2439 |

\* cited by examiner

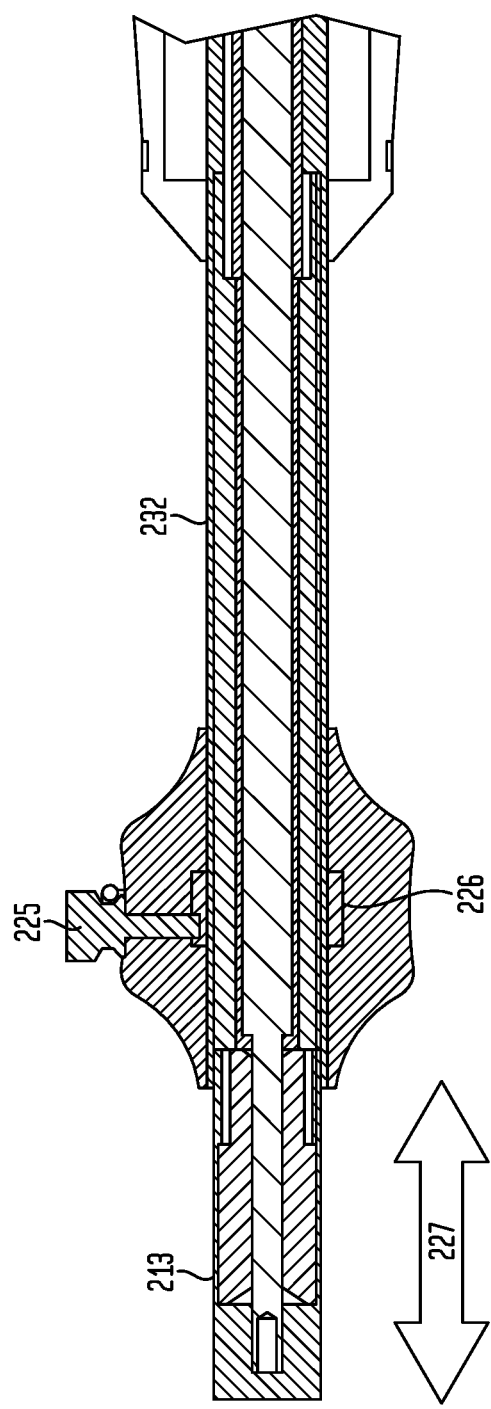

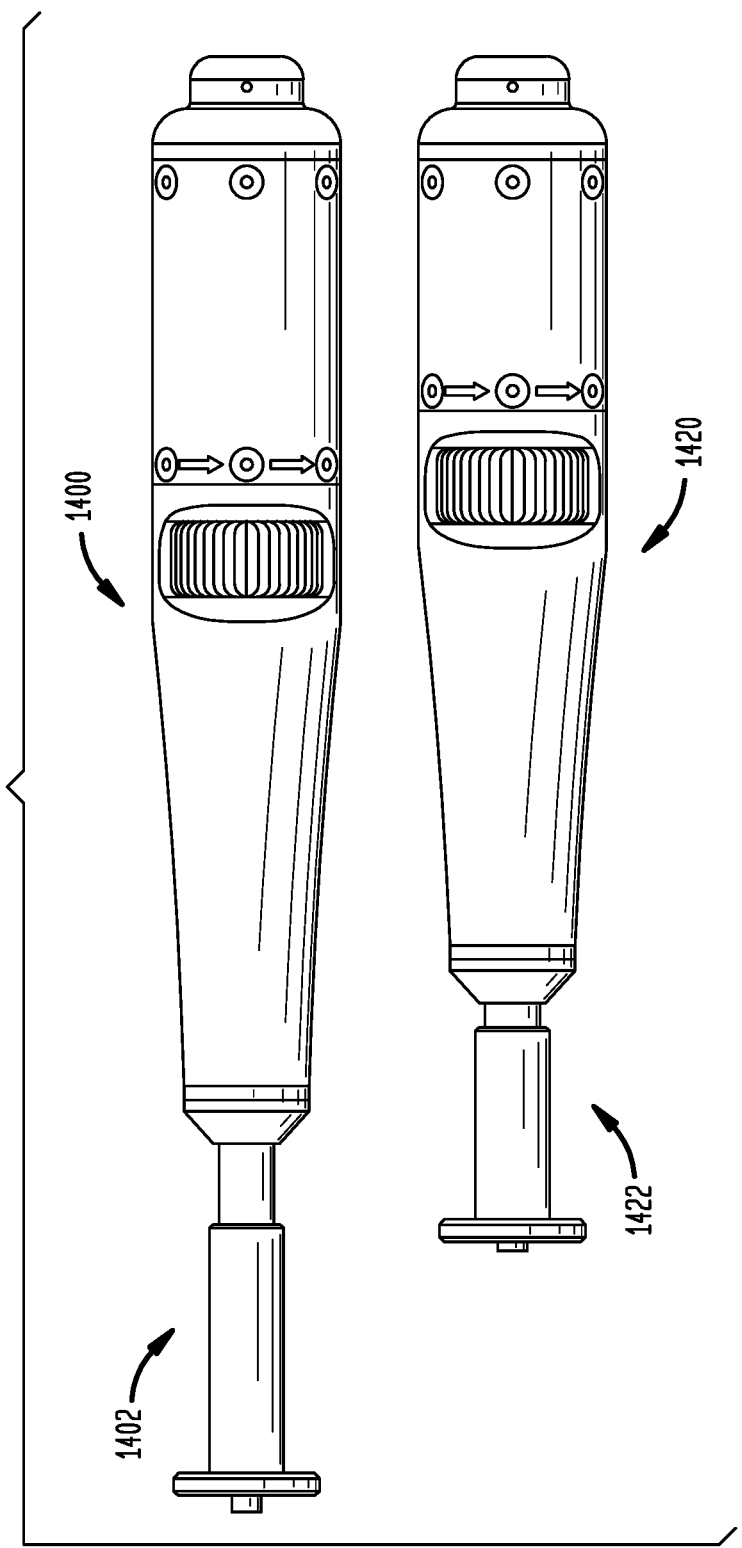

CARDIAC VALVE LOADING DEVICES AND SYSTEMS

CROSS-REFERENCE TO RELATED APPLICATIONS

This application claims the benefit of the filing date of U.S. Provisional Patent Application No. 62/750,731, filed on Oct. 25, 2018, the disclosure of which is hereby incorporated herein by reference.

BACKGROUND OF THE INVENTION

The present invention relates generally to the treatment of cardiac valve disorders, such as mitral valve replacement, using minimally invasive techniques. In particular, this application is directed towards devices for delivering and placing replacement mitral valves.

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

During minimally invasive procedures for mitral valve replacement, the mitral valve prosthesis generally must be collapsed into a small delivery device for placement within the native mitral valve orifice. Such collapsing can be difficult and time-consuming. Safe and efficient delivery systems, loading devices, and methods for replacement of a cardiac valve that address some or all of these concerns are described herein.

BRIEF SUMMARY OF THE INVENTION

A loading device configured to radially collapse an expandable medical implant may include an operating handle having an opening therein extending along a longitudinal axis thereof, a native sheath having a proximal end coupled to a distal end of the operating handle and partially extending into the opening of the operating handle, such that the native sheath is configured to translate relative to the operating handle parallel to the longitudinal axis, a removable sheath having a proximal end removably coupled to a distal end of the native sheath, an actuation rod extending parallel to the longitudinal axis at least partially through the opening of the operating handle, a lumen of the native sheath, and a lumen of the removable sheath, a distal end of the actuation rod being configured to be removably coupled to the expandable medical implant, and a first control element movable relative to the operating handle and coupled to the native sheath, the first control element being configured to translate the native sheath and the removable sheath relative to the operating handle in first and second longitudinal directions parallel to the longitudinal axis.

The loading device may also include a threaded rod extending within the opening parallel to the longitudinal axis and affixed to the native sheath. The first control element may be a sheathing knob threadedly engaged with the threaded rod, such that rotational motion of the sheathing knob causes the threaded rod, the native sheath, and the removable sheath to translate in one of the first or second longitudinal directions. The loading device may also include a second control element movable relative to the operating handle and coupled to the actuation rod. The second control element may be configured to translate the actuation rod relative to the operating handle in the first and second longitudinal directions. The loading device may also include a threaded rod extending within the opening parallel to the longitudinal axis and affixed to the actuation rod. The second control element may be a retention mechanism knob threadedly engaged with the threaded rod, such that rotational motion of the retention mechanism knob causes the actuation rod to translate in one of the first or second longitudinal directions.

The loading device may also include a ratchet and pawl mechanism that is coupled to the retention mechanism knob. The ratchet and pawl mechanism may be configured to permit rotation of the retention mechanism knob only in a single rotational direction. The loading device may also include a coupling element extending around the proximal end of the removable sheath and the distal end of the native sheath. The coupling element may removably couple the removable sheath to the native sheath. The lumen of the removable sheath may define a funnel having a first diameter at a distal end of the removable sheath and a second diameter at the proximal end of the removable sheath, the first diameter being greater than the second diameter.

The removable sheath may have a flange at the distal end of the removable sheath, the flange having a distal-facing surface extending in a plane oriented substantially perpendicular to the longitudinal axis, the flange having a through-opening that defines the first diameter at the distal end of the removable sheath. The actuation rod may have a threaded feature at the distal end thereof that is configured to be mated with a corresponding threaded feature of a retention mechanism that is coupled to the expandable medical implant. A medical combination may include the loading device described above, the expandable medical implant, and a retention mechanism removably coupling the expandable medical implant to the actuation rod of the loading device. The expandable medial implant may be radially collapsed within the lumen of the removable sheath.

Another loading device configured to radially collapse an expandable medical implant may include an operating handle having an opening therein extending along a longitudinal axis thereof, a brace coupled to the operating handle and configured to interface with a distal end of a delivery system configured to deploy the expandable medical implant, the brace having a lumen extending therethrough in a direction parallel to the longitudinal axis, a plurality of brace arms that extend between the brace and the operating handle, the brace arms configured to transfer a force acting on the brace along the longitudinal axis to the operating handle, a packing rod extending between the operating handle and the brace in first and second longitudinal directions parallel to the longitudinal axis, and a control element movable relative to the operating handle and coupled to the packing rod, the control element being configured to translate the packing rod relative to the operating handle and the brace in the first and second longitudinal directions.

The loading device may also include a threaded rod extending within the opening parallel to the longitudinal axis and affixed to the packing rod. The control element may be an actuation knob threadedly engaged with the threaded rod, such that rotational motion of the actuation knob causes the threaded rod and the packing rod to translate in one of the first or second longitudinal directions. The plurality of brace arms may include three brace arms that are circumferentially spaced apart from one another about the longitudinal axis, and one of the three brace arms may be configured to be selectively uncoupled from the operating handle and the brace.

The lumen of the brace may define a funnel having a first diameter at a proximal end of the brace and a second diameter at a distal end of the brace, the first diameter being greater than the second diameter. The brace may have a flange at the proximal end of the brace. The flange may have a proximal-facing surface extending in a plane oriented substantially perpendicular to the longitudinal axis. The flange may have a through-opening that defines the first diameter at the proximal end of the brace. The packing rod may have a first outer diameter at a proximal end of the packing rod within the opening of the operating handle and a second outer diameter at a distal end of the packing rod within the lumen of the brace, the first diameter being greater than the second diameter.

A method of loading an expandable medical implant into a distal end of a delivery device may include inserting an outer sheath at the distal end of the delivery device into a lumen of a brace of a loading device, removably coupling a retention mechanism to an inner shaft extending along a longitudinal axis within the outer sheath of the delivery device, the retention mechanism coupling the expandable medical implant to the inner shaft, applying a force onto the retention mechanism, the applying including pressing a distal end of a packing rod of the loading device onto a distal end of the retention mechanism, the pressing including actuating a control element of the loading device to translate the packing rod relative to the loading device in a longitudinal direction parallel to the longitudinal axis, and inserting the expandable medical implant into the outer sheath of the delivery device while the distal end of the packing rod and the outer sheath of the delivery device are positioned within the lumen of the brace of the loading device, the inserting of the expandable medical implant including further translating the packing rod relative to the loading device and the outer sheath of the delivery device in the longitudinal direction.

The control element may be an actuation knob threadedly engaged with a threaded rod that is affixed to the packing rod, and the applying of the force onto the retention mechanism may include rotating the actuation knob. The lumen of the brace may define a funnel having a first diameter at a proximal end of the brace and a second diameter at a distal end of the brace, the first diameter being greater than the second diameter. The inserting of the expandable medical implant into the outer sheath may include collapsing the expandable medical implant in a plurality of radial directions perpendicular to the longitudinal axis while at least a portion of the expandable medical implant is positioned within the lumen of the brace. The method may also include removing the outer sheath of the delivery device from the lumen of the brace of the loading device, the expandable medical implant being disposed within the outer sheath in a collapsed state after the removing is completed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D show an exemplary loading device.

FIG. 14 show two exemplary loading devices.

DETAILED DESCRIPTION

The loading devices described herein can be used to load a wide variety of replacement heart valves (also referred to herein as "replacement valves" or "valve"), such as prosthetic valves, into one or more delivery systems. Exemplary prosthetic valves that can be delivered and deployed with the delivery devices described herein include the expandable prosthetic valves described in application Ser. No. 14/677,320, filed Apr. 2, 2015, in U.S. Pat. No. 8,870,948, and in International Patent Application filed May 13, 2016, titled "REPLACEMENT MITRAL VALVES," and in U.S. patent application Ser. No. 14/677,320, filed Apr. 2, 2015, titled "REPLACEMENT CARDIAC VALVES AND METHODS OF USE AND MANUFACTURE," all of which are incorporated by reference herein. For example, the loading devices herein are configured to deliver and deploy a replacement heart valve, such as a mitral valve, that includes distal and proximal anchors.

The loading devices and methods described herein can be used to load replacement valves into a delivery system, which can then be used to deliver the replacement valves into patients. In some embodiments, the loading devices can be used to load replacement valves into a trans-septal delivery system, which may be used to compensate for a force required to load a long, flexible catheter such as that used for a trans-septal delivery system. In some cases, the loading devices can be used to compensate for the force required to load a replacement valve, which may be difficult to achieve with a long, flexible catheter such as that used for a trans-septal delivery system. For example, it may be difficult for a long flexible device to apply the necessary forces since flexibility of a device may compromise other characteristics, like tensile strength. The loading devices may be suitable for use with any type of replacement heart valve, including replacement mitral valves.

Figure 1:
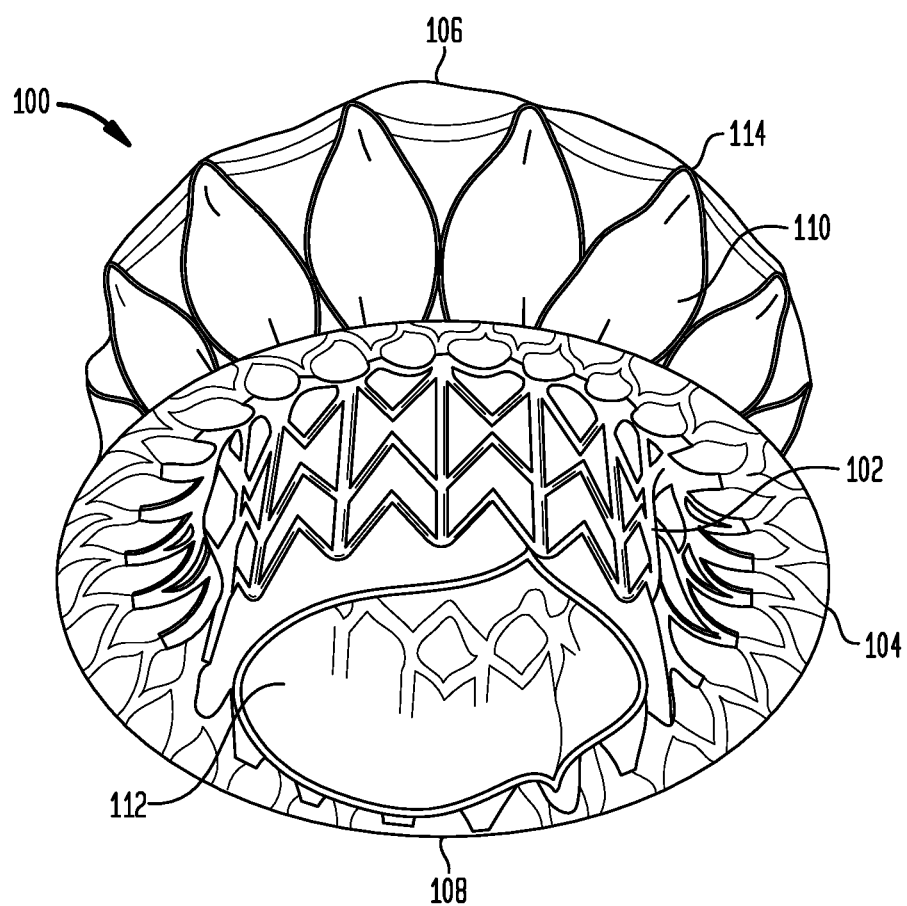
FIG. 1 shows a perspective view of a replacement mitral valve.

FIG. 1 shows a perspective view of a replacement mitral valve 100, in accordance with some embodiments. The valve 100 can include an inner strut frame 102 and an outer anchor assembly 104, which can cooperate to form a rigid support structure having an atrial side 106 and a ventricular side 108. In some embodiments, a skirt 110 covers outer surfaces of the support structure, and one or more leaflets 112 are positioned within a central channel of the support structure. Petals 114 of the outer anchor assembly 104 can be configured to collapse to reduce an outer diameter of the support structure when the support structure is loaded into the loading device and/or delivery system. When the valve 100 is in an expanded state, the petals 114 of both the atrial side 106 and a ventricular side 108 are fully extended radially outward, as shown in FIG. 1. The valve 100 is naturally in an expanded state when no force is applied to the petals 114. When the valve 100 is in a collapsed state, the petals 114 of both the atrial side 106 and a ventricular side 108 are at least partially collapsed radially inward. The valve 100 can be placed in a collapsed state by applying pressure onto the petals 114 in a radially inward direction. In a collapsed state, the valve 100 has a higher degree of potential energy (e.g., is spring loaded) compared to when the expanded state.

According to some embodiments, the loading device as described herein is configured to load a valve (e.g., valve 100) into an intermediate device that maintains the valve in a collapsed state prior to being transferred into the delivery system. These embodiments are described herein with reference to FIGS. 2A-9 and 14. According to some embodiments, the loading device is configured to load the valve directly (e.g., in an expanded state) into the delivery system. These embodiments are described herein with reference to FIGS. 10A-13 and 16A-16D.

Figure 2A:
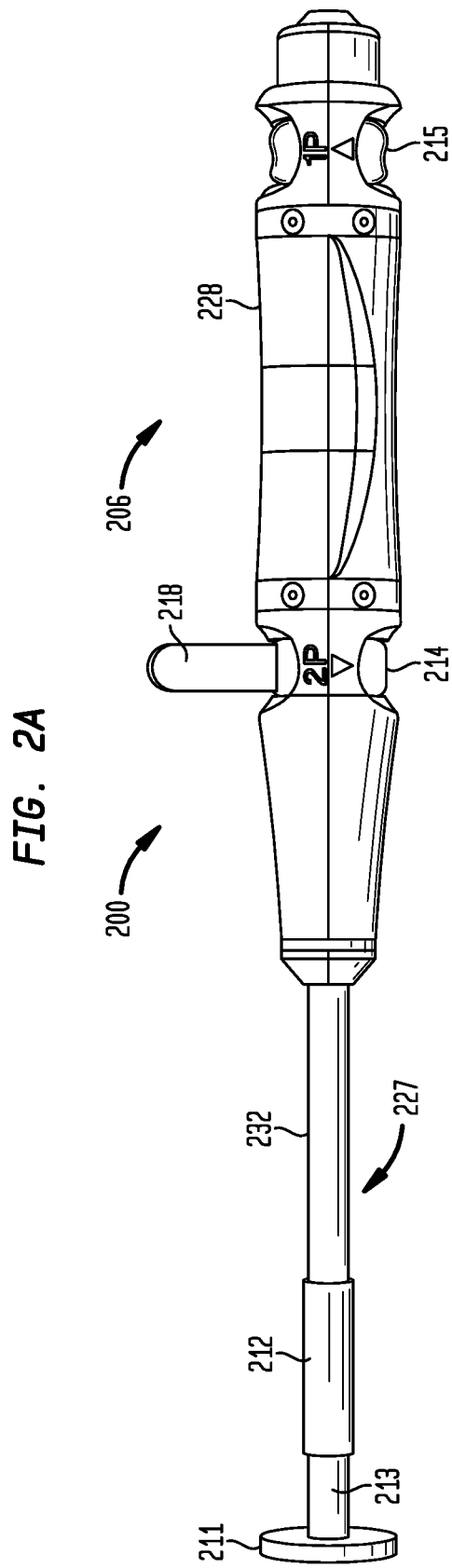
Figure 2B:
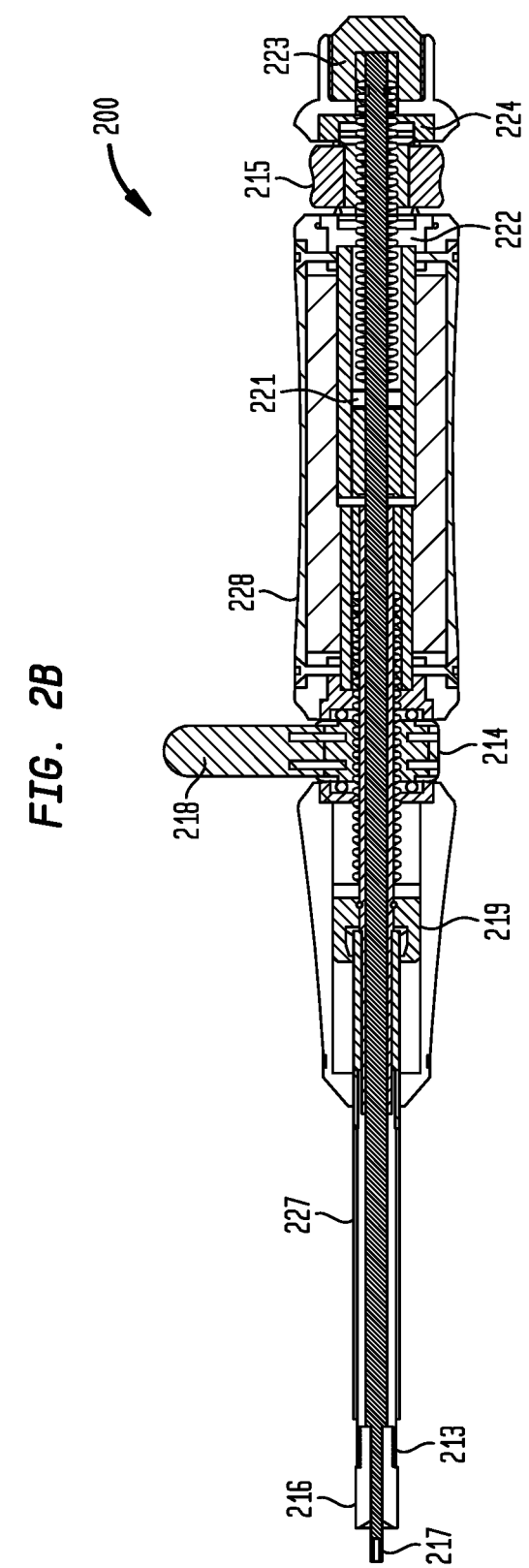
Figure 2D:
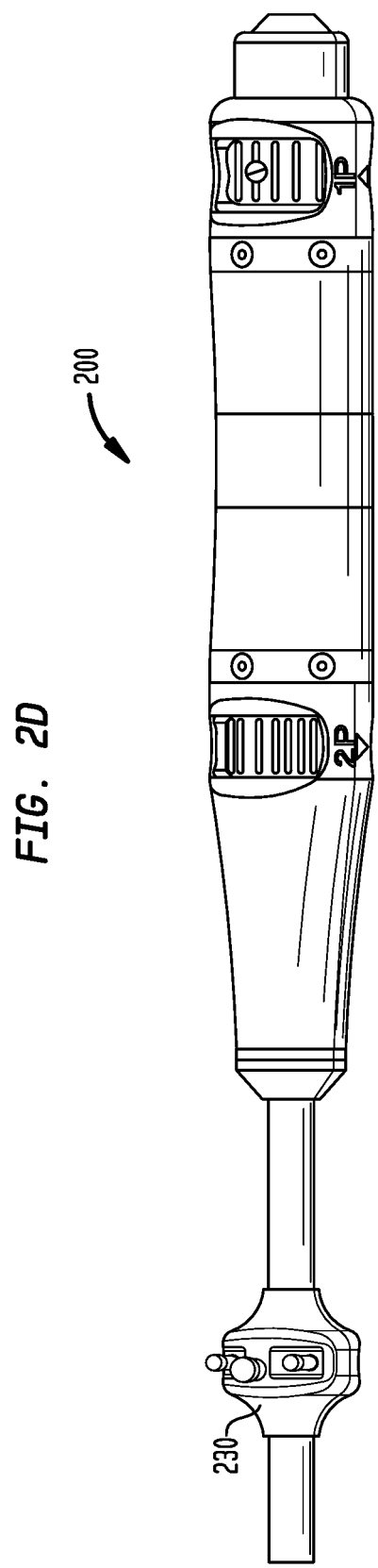

FIG. 2A-2D show an exemplary loading device 200, which includes various features for placing a valve in a collapsed (high energy) state. FIG. 2A shows a perspective view, FIG. 2B shows a longitudinal section view, FIG. 2C shows a close up longitudinal section view, and FIG. 2D shows an alternative perspective view of the loading device 200.

Referring to FIGS. 2A and 2B, the loading device 200 can include a handle 228 suitable for a user's hand, and an elongate body 227 with a central channel that is configured to secure the valve (not shown) therein for placement within a delivery system (not shown). The elongate body 227 can include one or more sheaths, including a native sheath 232, a removable sheath 213 (also referred to as a tube or funnel) and a shim sheath 212. The native sheath 232 may be securely attached to the handle 228. For example, the native sheath 232 can be positioned at least partially within the handle 228 and be configured to move relative to the handle 228. In some cases, the native sheath 232 is attached to a sheath adapter using, for example, a leadscrew. The removable sheath 213 may be removable from the handle 228, and be adapted to hold the valve therein. The shim sheath 212 can be used to allow compatibility with different diameters of sheaths and can slide over the native sheath 232 and/or the removable sheath 213. The loading device 200 can be adapted to secure the valve in a collapsed state.

The distal end of the removable sheath 213 can have a flange 211 that can be configured to provide smooth entry of the valve with minimal valve contact. The central channel of the elongate body 227 can include an actuation tube 217 (or rod) that engages with a retention mechanism that is coupled to the valve. In some embodiments, the actuation tube 217 includes a threaded inner or outer surface to provide secure engagement with the retention mechanism.

The tip 216 of the elongate body 227 can have features therein (e.g., on the inner diameter thereof) to guide the valve retention mechanism. For example, the tip 216 may have a funnel shape for guiding the valve retention mechanism and/or align the actuation tube 217 therein. The handle 228 can include a sheathing knob 214 (or first control element) to control actuation of the removable sheath 213. In some embodiments, rotation of the sheathing knob 214 can cause a translation motion of a sheath adaptor 219 and the actuation tube 217 in a longitudinal direction. In some embodiments, a torque bar 218 can be used for added mechanical advantage when turning the sheathing knob 214. In some embodiments, the torque bar 218 is removable. The handle 228 can include a retention mechanism knob 215 (or second control element) for controlling the retention mechanism. For example, the retention mechanism knob 215 may allow a user to switch between a first mode where the retention mechanism extended, and a second mode wherein the retention mechanism is retracted. In some cases, this may provide finer control of the retention mechanism. For example, this may allow for partial unsheathing of a valve if, for instance, it is determined that the valve is not collapsing correctly (e.g., unsymmetrically). The handle 228 may include proximal and distal race plates 224 and 222, which may be configured to ensure unidirectional travel (e.g., via a ratchet mechanism) and/or be configured to provide audible feedback to a user (e.g., via a pawl mechanism). A proximal terminator 223 and a proximal stop 221 may be configured to control limits of translation of the actuation tube 217.

The close up view of FIG. 2C shows a variation of the device 200 that includes flanges 226 on the elongate body 227. The flange(s) 226 may have one or more bosses that are adapted to allow partnered translation 227 of the removable sheath 213 with respect to the native sheath 232. This can allow for both loading and unloading forces to be applied to the removable sheath 213 without losing tension on the retention mechanism during loading of the valve. In some embodiments, a center screw 225 can be adapted to limit (e.g., prevent) rotation of the removable sheath 213 relative to the native sheath 232. FIG. 2D shows an optional sheath adapter 230, which can be used to allow for different sized sheaths as an alternative to using the shim sheath 212 (FIG. 2A).

Figure 3A:
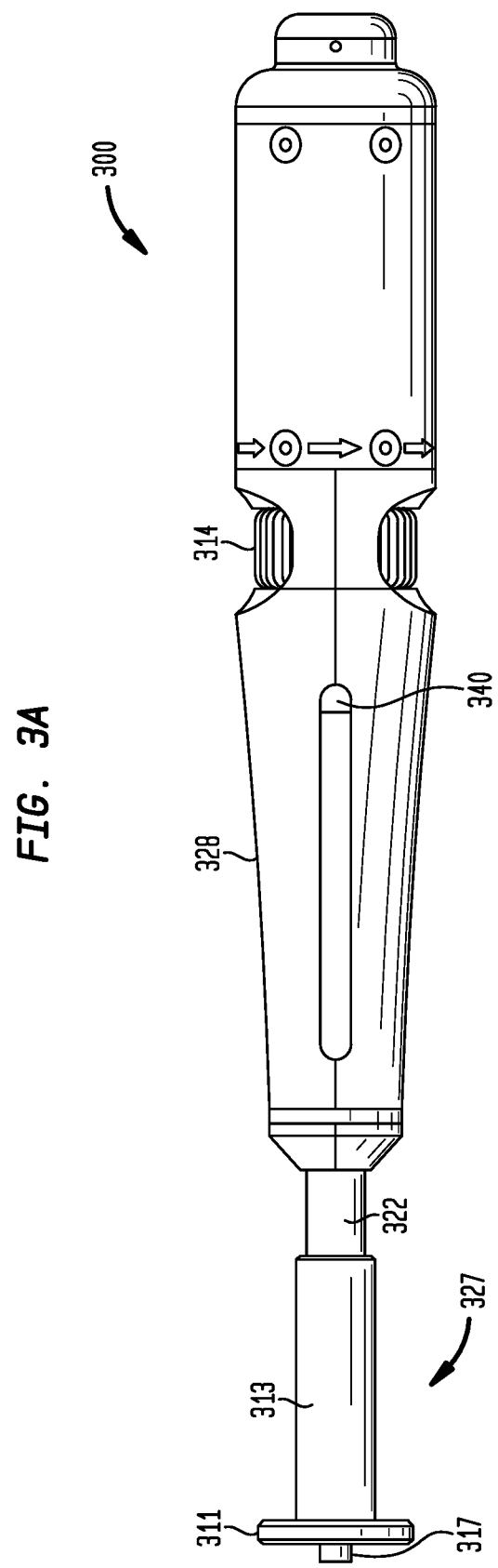
FIGS. 3A-3B show another exemplary loading device.
Figure 3B:
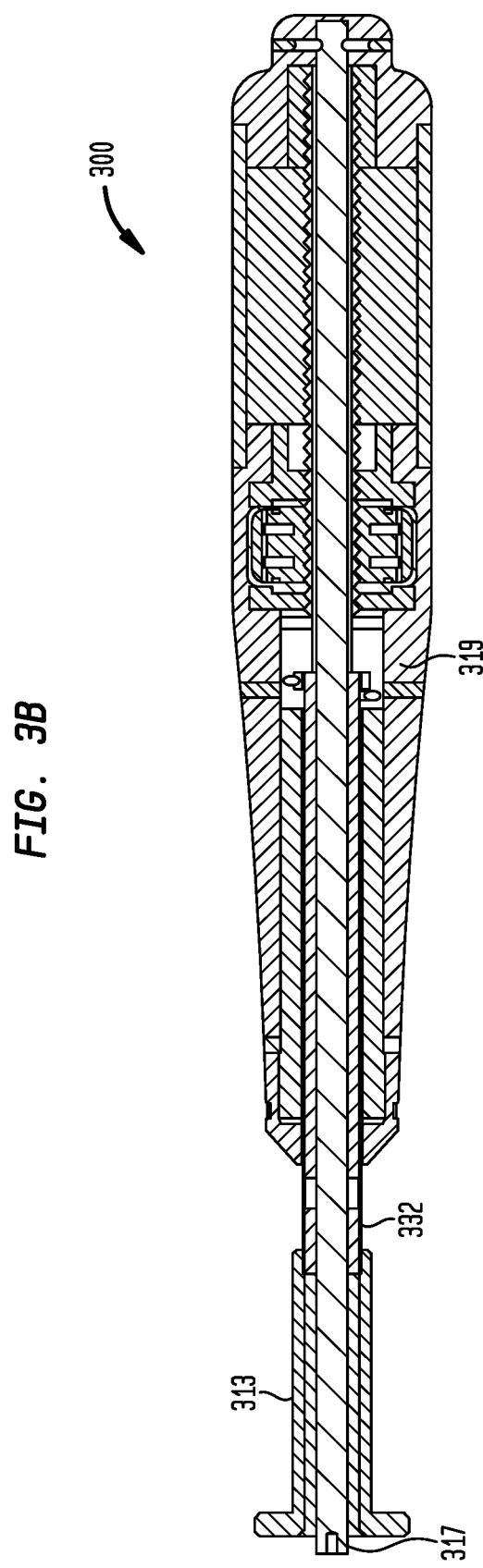

FIGS. 3A and 3B show perspective and longitudinal section views, respectively, of a loading device 300. The loading device 300 has many similar features as the loading device 200 (FIGS. 2A-2D). For example, the loading device 300 can include a handle 328 and an elongate body 327 having a central channel. The elongated body can include a native sheath 332 and a removable sheath 313. The removable sheath 313 can have a flange 311 that can be configured to provide smooth entry of the valve with minimal valve contact. An actuation tube 317 (or rod) can be configured to engage with a retention mechanism coupled with the valve. A sheathing knob 314 can be configured to control actuation of the removable sheath 313. In some embodiments, rotation of the sheathing knob 314 can cause a translation motion of a sheath adaptor 319 in a longitudinal direction. In some embodiments, the handle 328 includes an indicator, which can be operationally coupled with the sheathing knob 314 to indicate to a user whether the loading device 300 is ready for loading a valve assembly.

The loading device 300 may be configured to perform the entire collapse and covering of the valve. According to some embodiments, the loading device 300 does not include a separate retention mechanism knob (e.g., retention mechanism knob 215 of FIGS. 2A-2B). In some situations, this may provide more ease and convenience for loading the valve. This may also provide a more simple assembly process for manufacturing the loading device (e.g., reduction in parts).

Figure 3C:
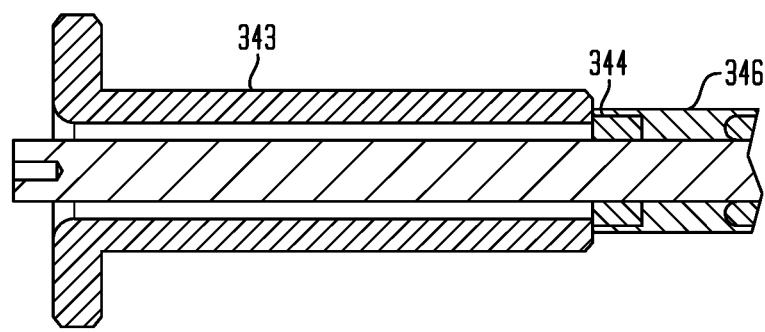
FIGS. 3C-3D show exemplary portions of a loading device.
Figure 3D:
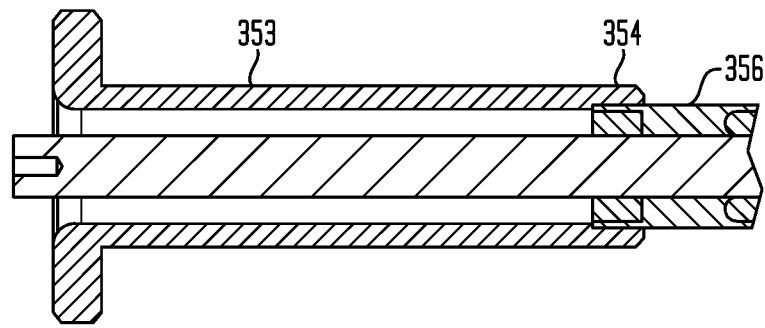

The removable sheaths (also referred to as funnels) described herein can be adapted to cooperate with delivery systems having elongated bodies (e.g., outer sheaths) of different diameters. The removable sheaths may be adjustable to match different catheter sizes without changing the loading tool (e.g., versus emphasis on matching various loading tools). This way, the removable sheath can be modified to fit any of a number of different delivery systems while maintaining compatibility with a single loading tool configuration. FIGS. 3C and 3D show longitudinal section views of exemplary removable sheaths having different interface features. In FIG. 3C, the removable sheath 343 has an inner diameter portion 344 that has a smaller or equal outer diameter compared to the inner diameter of the corresponding native sheath 346. The inner diameter portion 344 of the removable sheath 343 may also be adapted to interface with a corresponding portion of the delivery system (e.g., an outer sheath). In FIG. 3D, the removable sheath 353 has an inner diameter portion 354 that has a larger outer diameter compared to the inner diameter of the corresponding native sheath 356. The inner diameter portion 354 of the removable sheath 353 may also be adapted to interface with a corresponding portion of the delivery system (e.g., an outer sheath).

A valve can be loaded onto a loading device (e.g., loading devices 200 or 300) in a number of stages. FIGS. 4A-4D shows an example of multiple phases of loading a valve holder assembly 420 into a loading device, according to some embodiments. One or more of the operations shown in FIGS. 4A-4D can be performed while the valve and/or loading device (or a portion thereof) is/are submerged in a solution (e.g., saline solution).

Figure 4A:
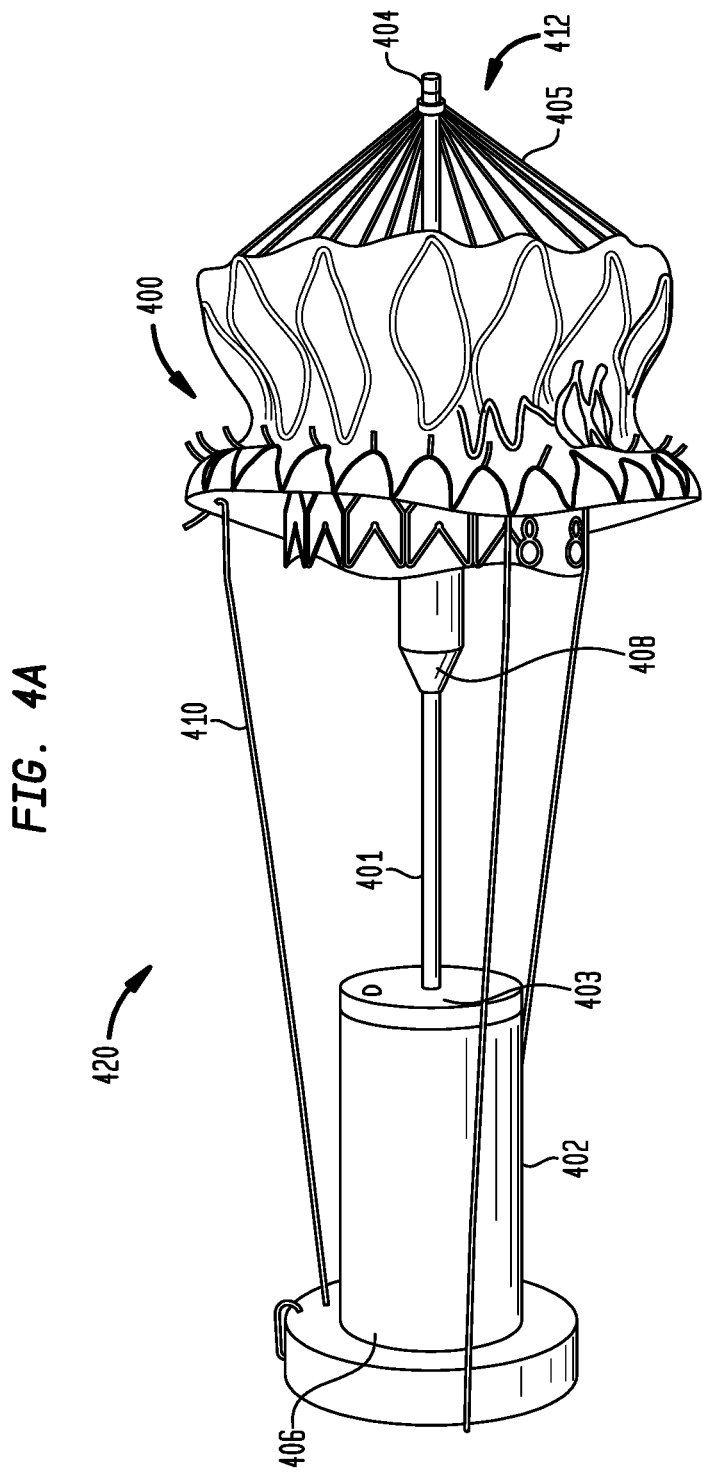
FIGS. 4A-4D show exemplary valve holder assemblies and loading devices.

Referring to FIG. 4A, to prepare the valve for loading, the ventricular side of the valve 400 can be coupled to a valve holder 402, and the atrial side of the valve can be coupled to a retention mechanism 412 (also referred to as a suture ring and/or a florette), which may include or be coupled to a first hypotube 404. On the ventricle side, the valve holder can include a second (e.g., larger) hypotube 401 that can be used to control (e.g., prevent) rotation of the valve 400 during loading. The first hypotube 404 and/or the second hypotube 401 may be centrally located with respect to the valve holder assembly 420 and may be made of a corrosion resistant material, such as stainless steel. The second hypotube 401 can be coupled to a stand 406, which a user can hold in place or twist during loading. The valve support 408 can be used to assure proper positioning of the valve 400. The second hypotube 401 can be configured to set the distance of a valve support 408 (also referred to as a spacer) relative to the valve holder 402, so that the valve 400 can collapse at a correct height relative to the valve support 408. The second hypotube 401 may be affixed to the valve support 408. For example, the second hypotube 401 can dictate the distance of the valve support 408 from the face 403 of the valve holder 402, to control how and/or where the valve 400 is supported.

One or more retainers 410 (e.g., 2, 3, 4 or more retainers), which can correspond to wires, can be used to couple the petals of the ventricular side of the valve 400 to the valve holder 402. In some embodiments, the retainers 410 are have hooks that attach to the petals of the ventricular side. In some cases, hooks of the retainers 410 poke through the skirt of the valve. The retainers 410 (and in some cases other metal portions of the valve holder assembly) are made of a corrosion resistant material (e.g., nickel titanium). In some cases, the retainers 410 are made of material that is non-reactive with the inner strut frame of the valve 400, since retainers 410 may directly contact the inner strut frame of the valve 400 during the valve collapsing process. On the atrial side, the retention mechanism 412 may be part of or be coupled to the hypotube 401. In some embodiments, the retention mechanism 412 corresponds to or includes a ring having a central opening that communicates with a central opening of the hypotube 401. The retention mechanism 412 can include one or more sutures 405 (also referred to as threads) that is/are threaded therethrough. The sutures 405 can be tethered to (e.g., looped through) a corresponding petal of the atrial side and interact with features therein. For example, the sutures 405 may loop around pins on the petals. In some embodiments, the sutures 405 are threaded through the skirt of the valve. In some embodiments, the sutures 405 are one continuous thread. Tension may be placed on the sutures 405 to provide control during the loading process. In some cases, the ends of the sutures 405 are pinched (e.g., crimped) to prevent possible hooking onto other features of the valve holder assembly. In some cases, the crimps or coils on sutures 405 are secured in place by an adhesive, which can help maintain tension and avoid inadvertent separation of the sutures 405.

Figure 4B:
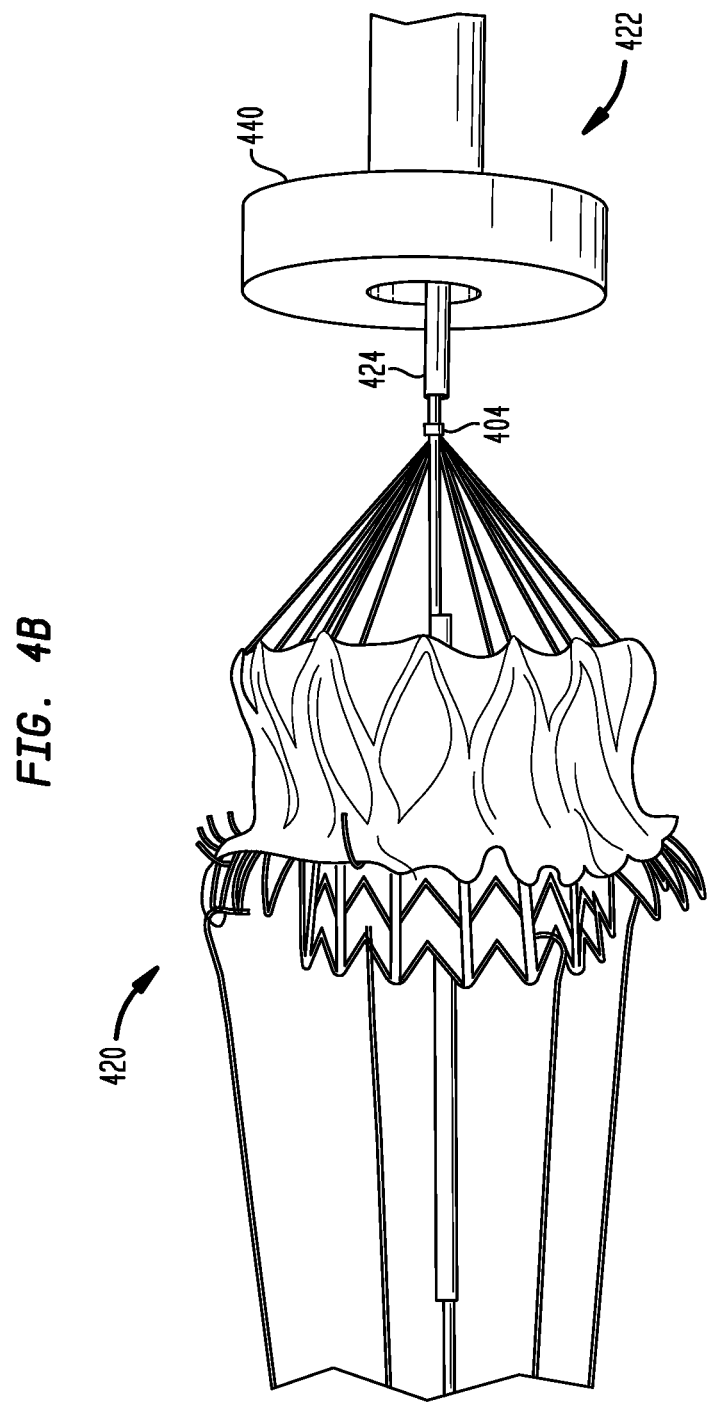

Once the valve 400 is attached to the valve holder, this assembly can be coupled to the loading device. FIG. 4B shows a valve holder assembly 420 being loaded onto a loading device 422, in accordance with some embodiments. The tip of the retention mechanism 412 can be coupled to an actuation tube 424 positioned within a channel of the removable sheath 440 of the loading device 422. In some embodiments, the retention mechanism 412 is screwed onto the actuation tube 424 by twisting the stand 406 (FIG. 4A). After securing the valve holder assembly 420 and the loading device 422, a sheathing knob of the loading device can be rotated to pull the actuation tube 424 and the retention mechanism 412 proximally toward the loading device 422. Since the valve holder assembly 420 and loading device 422 are held in place, a resulting tension placed on the petals of the atrial side of the valve the causes the petals to partially collapse radially inward.

Figure 4C:
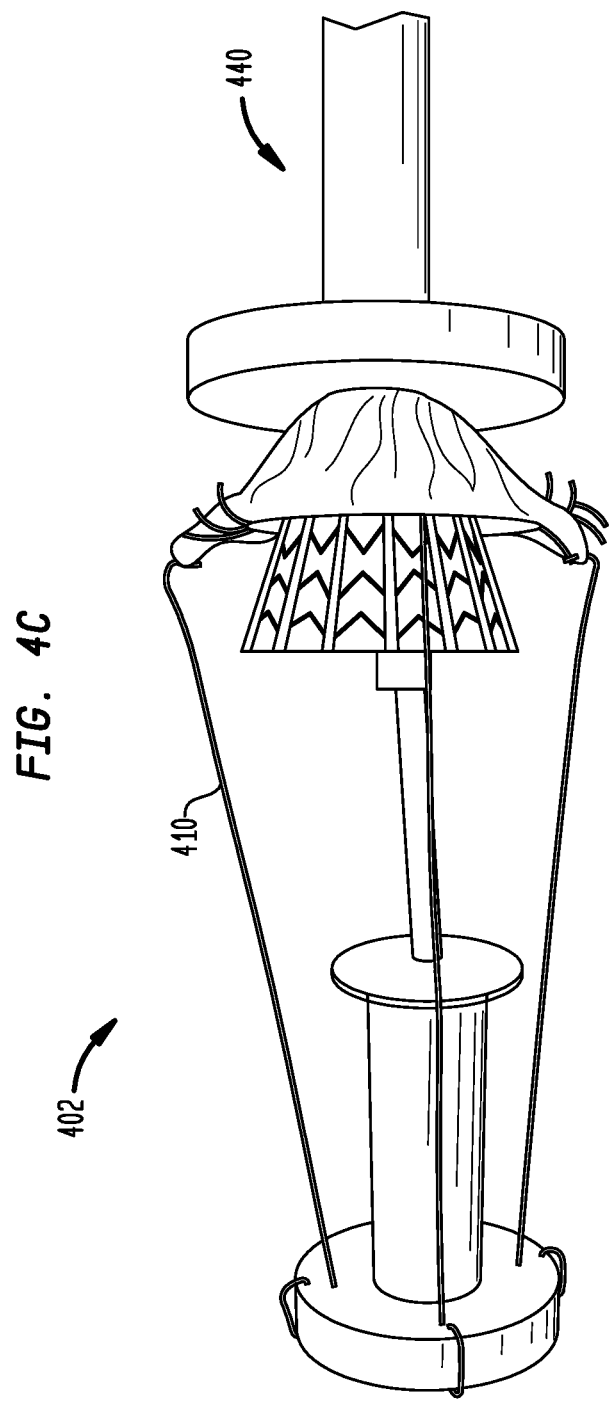
Figure 4D:
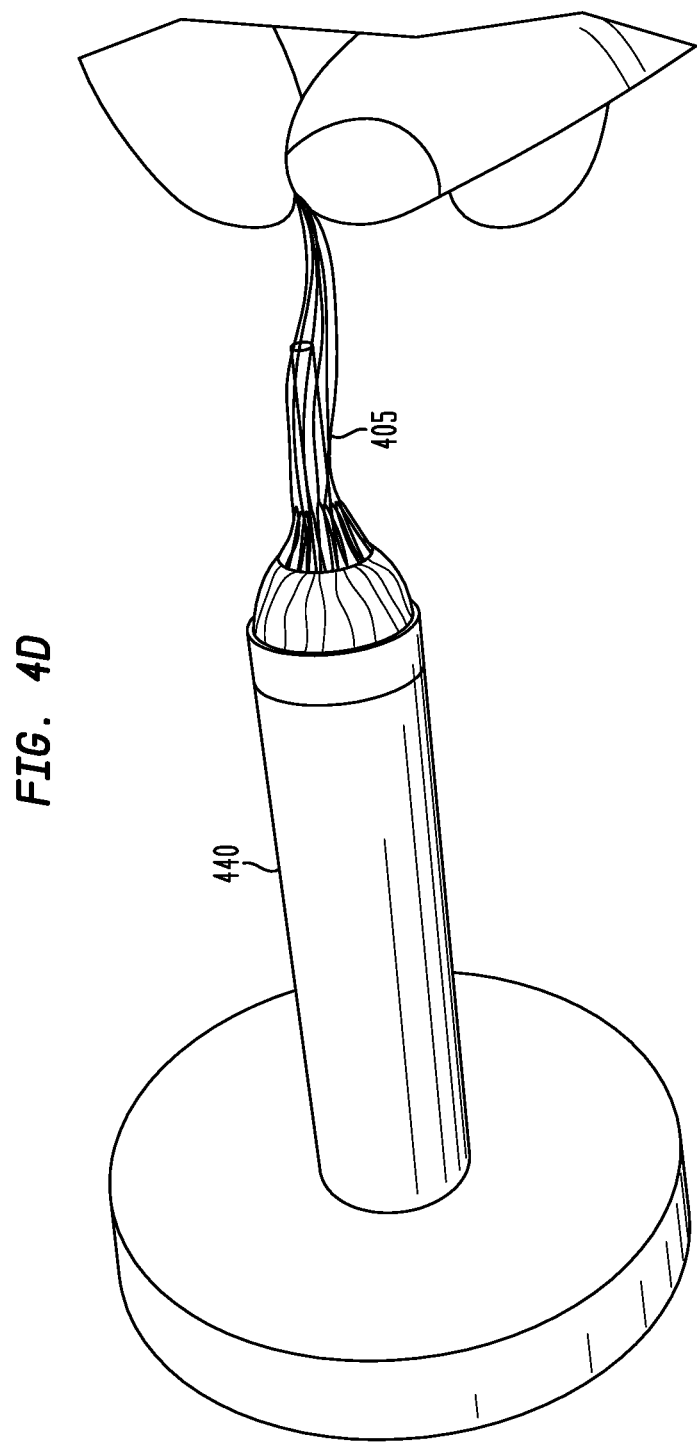

As shown in FIG. 4C, the sheathing knob of the loading device can continued to be rotated until the atrial petals collapse radially inward to an extent sufficient for the atrial side of the valve 400 to enter the channel of the removable sheath 440. The retainers 410 can then be removed from ventricular side of the valve 400. The sheathing knob of the loading device can continued to be rotated until the valve 400 is fully enclosed within the removable sheath 440. The removable sheath 440, with the collapsed valve inside, can then be removed from the loading device for loading into the delivery system (i.e., from the removable sheath), as show in FIG. 4D. The hypo-tubes 401 and 404 and valve support 408 can also be configured to be withdrawn and removed. In some cases, the sutures 405 remain coupled to the valve during installation into the delivery system. Apparatuses and method for loading a valve into a delivery system may be described in International Patent Application No. PCT/US2016/032546 and U.S. Provisional Application No. 62/424,051, each of which is incorporated by reference herein in its entirety.

Figure 5:
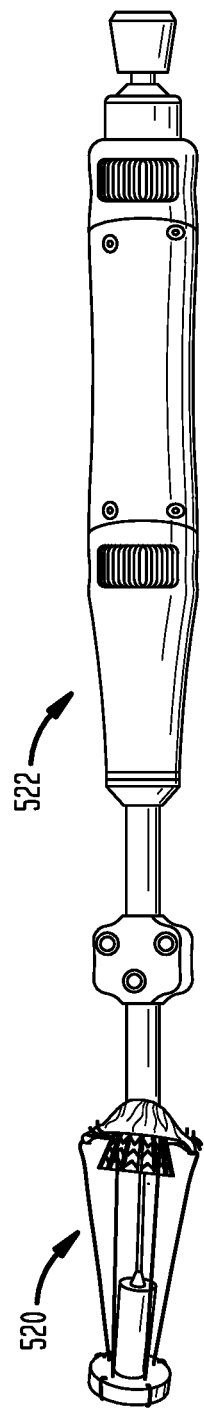
FIGS. 5 and 6 show exemplary valve holder assemblies attached to loading devices.
Figure 6:
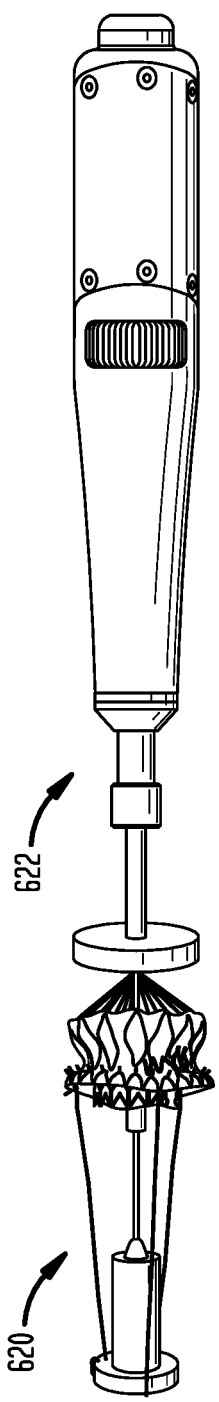

FIG. 5 shows a perspective view of a valve holder assembly 520 that can be loaded into a loading device 522 having sheathing knob and a retention mechanism knob. FIG. 6 shows a perspective view of a valve holder assembly 620 that can be loaded into a loading device 622 having sheathing knob (i.e., without a retention mechanism knob).

Figure 7A:
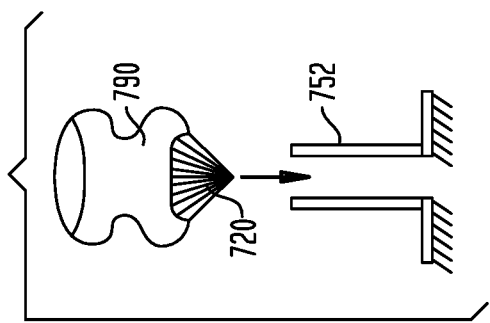
FIGS. 7A-7C show an exemplary process for using a chaser tube.
Figure 7B:
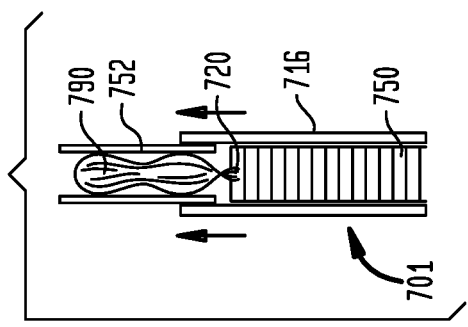
Figure 7C:
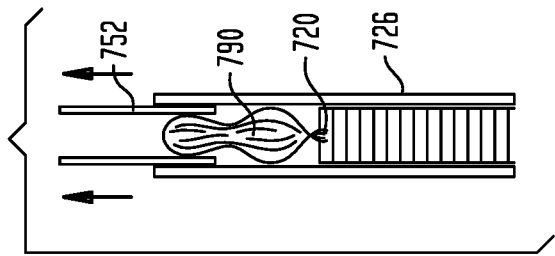

In some embodiments, the valve can be loaded into the delivery system from an elongated tube, referred to as a chaser tube. An exemplary loading device in the form of a chaser tube 752 is shown in FIGS. 7A-7C. The valve 790 can be loaded into the chaser tube 752. In some cases, a loading tool is used to position the valve 790 into chaser tube 752. The atrial side of the valve 790, including the retaining mechanism 720 (e.g., florette), can be installed into the chaser tube 752 first. This can be accomplished by pulling the retaining mechanism (e.g., manually or automatically) until the petals of the valve collapse and the valve takes on a smaller diameter, as described herein. As shown in 7B, the chaser tube 752 can have a diameter that is smaller than the inner diameter of an outer sheath 716 as part of a delivery system 701 (i.e., used to deliver the valve into a patient). In some embodiments, the outer sheath 716 corresponds to catheter (or a portion thereof). The chaser tube 752 can be positioned partially within the outer sheath 716 to align the chaser tube 752 and outer sheath 716. In some cases, the outer sheath 716 is pushed over the chaser tube 752. The retaining mechanism 720 can be coupled to a distal assembly 750 within the outer sheath 716 to maintain tension on the valve 790. When the chaser tube 752 is pulled (e g, manually or automatically), the valve 790 exits the chaser tube 752 and is retained within the outer sheath 716. In some cases, the valve 790 expands a little during this process. The chaser tube 752 can then be removed, leaving the valve 790 within the outer sheath 726.

Figure 8A:
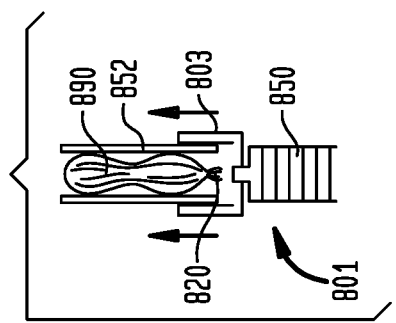
FIGS. 8A-8C show another exemplary process for using a chaser tube.
Figure 8B:
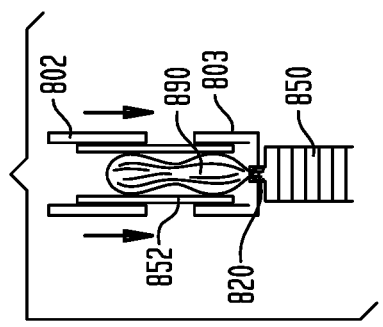
Figure 8C:
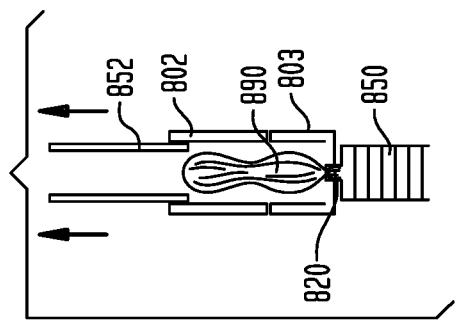

An exemplary use of a chaser tube 852 with a split sheath delivery system 801 is shown in FIGS. 8A-8B. A split sheath delivery system 801 can include a proximal sheath 803 and a distal sheath 802. As shown, the valve 890 can be loaded into the chaser tube 852, which can be placed inside the proximal sheath 803. The retaining mechanism 820 (e.g., florette) can then be attached to the distal assembly 850, and the distal sheath 802 can be pulled over the distal portion of the chaser tube 852. In some embodiments, a threaded nose-cone tool is used to terminate the distal sheath 802 after transfer. Once the valve 890 is within the sheath 802, the chaser tube 852 can be removed.

Figure 9:
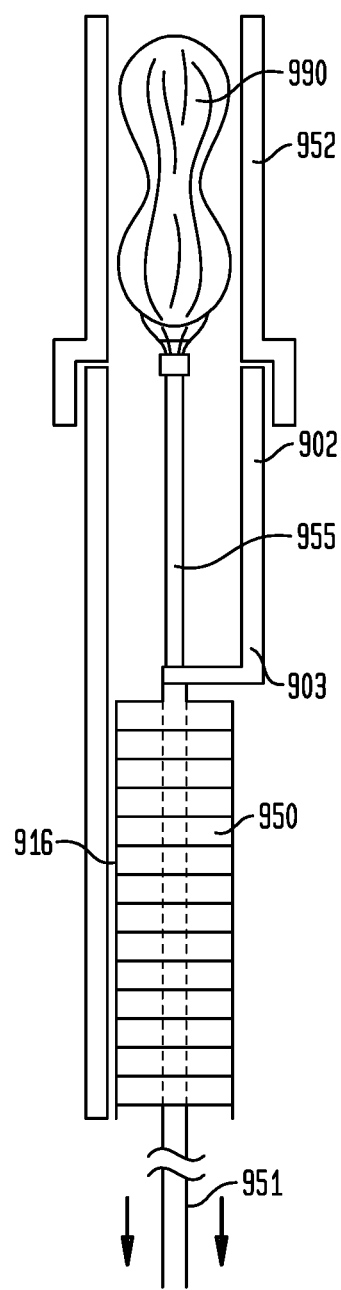
FIG. 9 shows another exemplary process for using a chaser tube.

Another embodiment of a chaser tube 952 is shown in FIG. 9. The chaser tube 952 can have a diameter that is substantially the same as the diameter of the sheath 916 (or the distal sheath 902 if a split sheath is used) and a proximal lip having a wider diameter so that it is configured to fit over the outer sheath 916 (and/or the proximal sheath 902 if a split sheath is used). The valve 990 can be loaded into the chaser tube 952. In some cases, a loading tool is used to position the valve 990 into chaser tube 952. The chaser tube 952 can then be aligned over the outer sheath of the delivery system. A pull system 955 can then be attached to the retaining mechanism (e.g., florette or first hypotube) of the valve assembly and pulled proximally to pull the valve 990 into the sheath 916 (or 902/903 if a split sheath) that is coupled to the catheter 950 as part of the delivery system. In some instances, the catheter 950 includes a layer of material therein to facilitate loading of the valve 990 within the delivery system.

FIGS. 10A-10E show various views of another exemplary loading device 1000, which can be configured to directly load a valve into a delivery system. The loading device 1000 may advantageously avoid the transfer steps of loading the valve in an intermediate device (e.g., removable sheath and/or chaser tube). In some cases, this can minimize corrosion of the valve. The loading device 1000 may include various valve tethering mechanisms, and may provide an internal support to collapse the valve in a symmetric, repeatable manner.

Figure 10A:
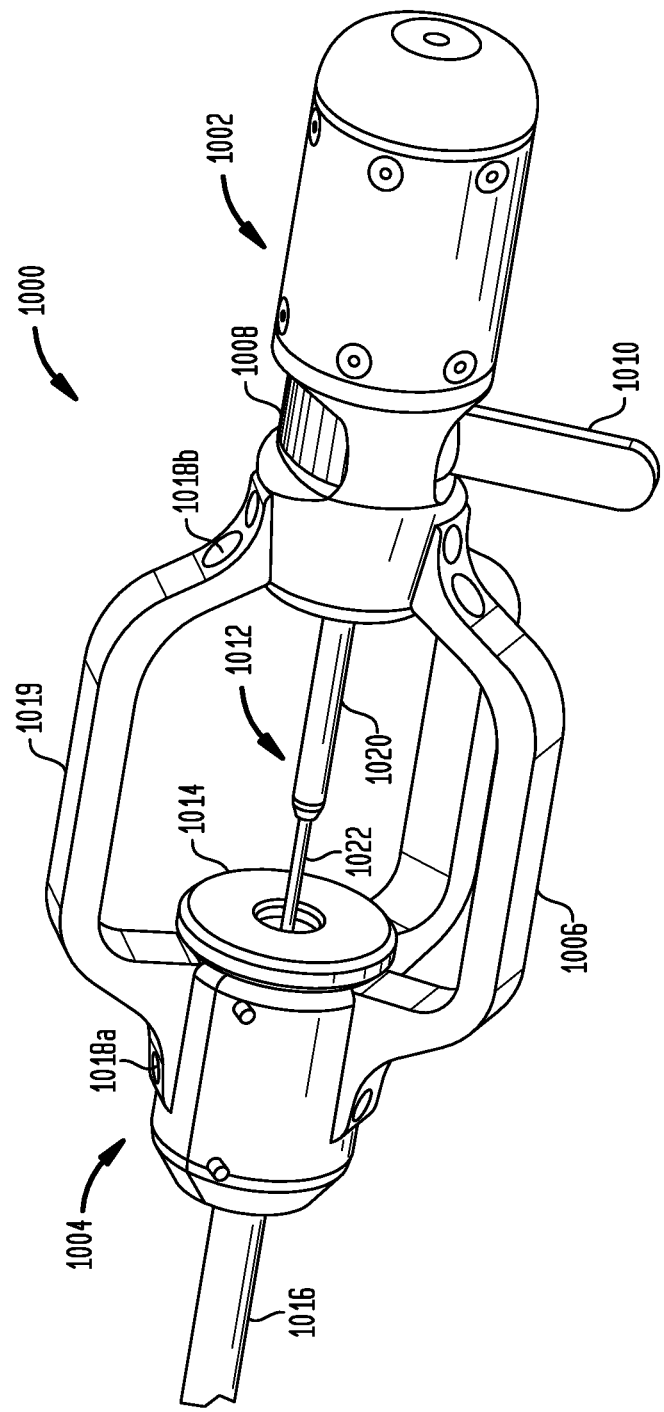
FIGS. 10A-10E show another exemplary loading device and process for using the loading device.
Figure 10B:
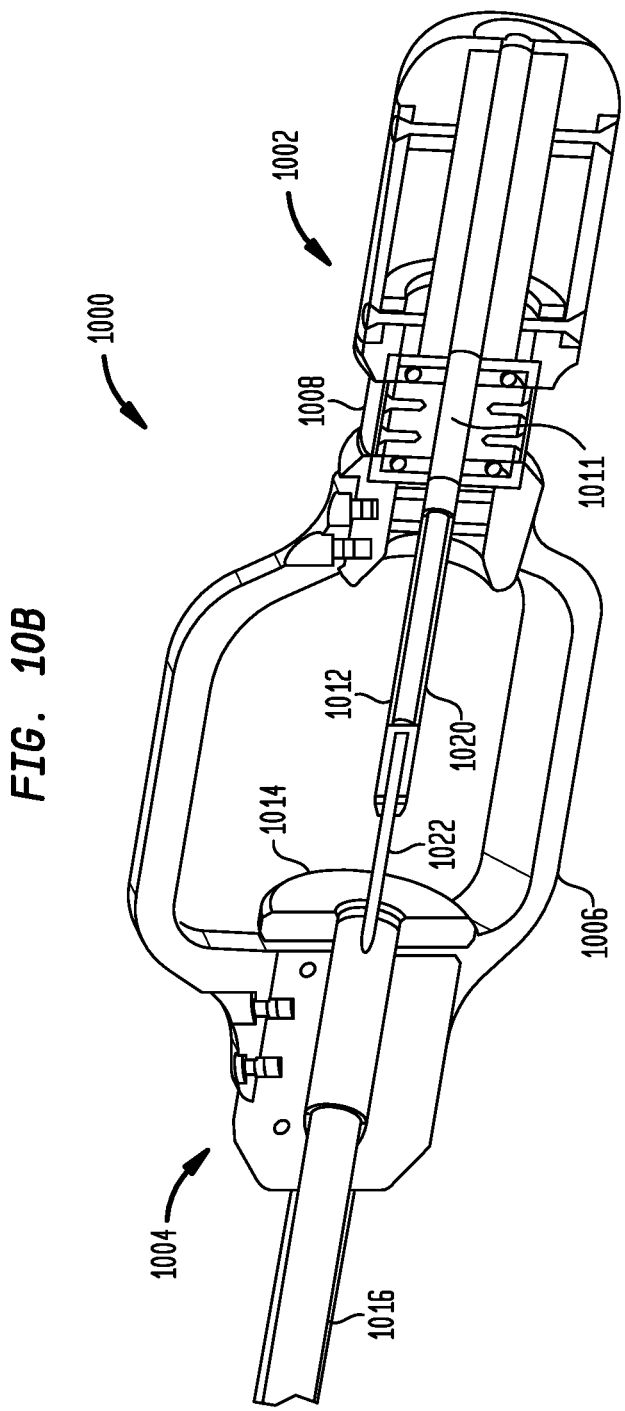

FIGS. 10A and 10B show a perspective view and longitudinal section view, respectively, of loading device 1000. The device 1000 can include a handle 1002 and a brace 1004, which can be configured to interface with a valve delivery system. For example, the brace 1004 can be configured to fit around a delivery catheter 1016 (e.g., that is part of the delivery system). A plurality (e.g., three) brace arms 1006, which extend from the brace 1004 to the handle 1002, can extend radially outward and transfer axial force from loading back to the handle 1002. This arrangement may prevent the force of loading from pushing the catheter 1016 and loading device 1000 apart. The plurality of brace arms 1006 can be spaced from one another so as to keep the valve from prevent loading on the valve while providing room to access the valve during its collapse. Thus, for example, in some embodiments, the brace arms 1006 can be positioned at about 150 degrees, 60 degrees, and 150 degrees apart, respectively. The device 1000 can include a flange 1014 radially inward of the brace arms 1006 and at a proximal end of the brace 1004. The flange 1014 can have an internal radius that guides the valve into the delivery catheter 1016. A packing rod 1012 can extend from the handle 1002 toward the brace 1004. The packing rod 1012 can include a proximal portion 1020 (proximal to the handle 1002) and a distal portion 1022. In some embodiments, the proximal portion 1020 has a larger outer diameter than that of the distal portion 1022 (e.g., tapers down). This configuration may reduce the occurrence of asymmetric valve collapse during loading. In some embodiments, the packing rod 1012 (or a portion thereof) can be replaced with a balloon.

In some embodiments, fasteners 1018*a* and 1018*b* (e.g., screws) can be used to secure and/or remove one of the bracing arms 1006 (e.g., arm 1019 that is about 150 degrees away from the other two arms). The one or more bracing arm 1006 may be removed in order to provide space for catheter insertion into the brace 1004 and can then be replaced by attachment with the fasteners 1018*a* and 1018*b*. The handle 1002 can include a knob 1008, and optionally a torque bar 1010, for controlling the loading process. The knob 1008 can be configured to turn a threaded rod 1011, which advances the packing rod 1012 to pack the valve into the delivery catheter 1016. Reversing the direction of the knob 1008 can retract the packing rod 1012 from the delivery catheter 1016.

In some embodiments, the delivery device 1000 can include a through-lumen extending through the handle 1002 and packing rod 1012. The through-lumen can be used, for example: (1) as a port to input saline for an internal support balloon (if replacing the packing rod 1012); (2) to allow a guidewire, mandrel, or other lumen to remain through the device 1000 prior to, during, or after loading of the valve without interrupting; and/or (3) to be used with a stabilizer or stand that would allow the valve to be attached to the loading device 1000 directly.

Figure 10C:
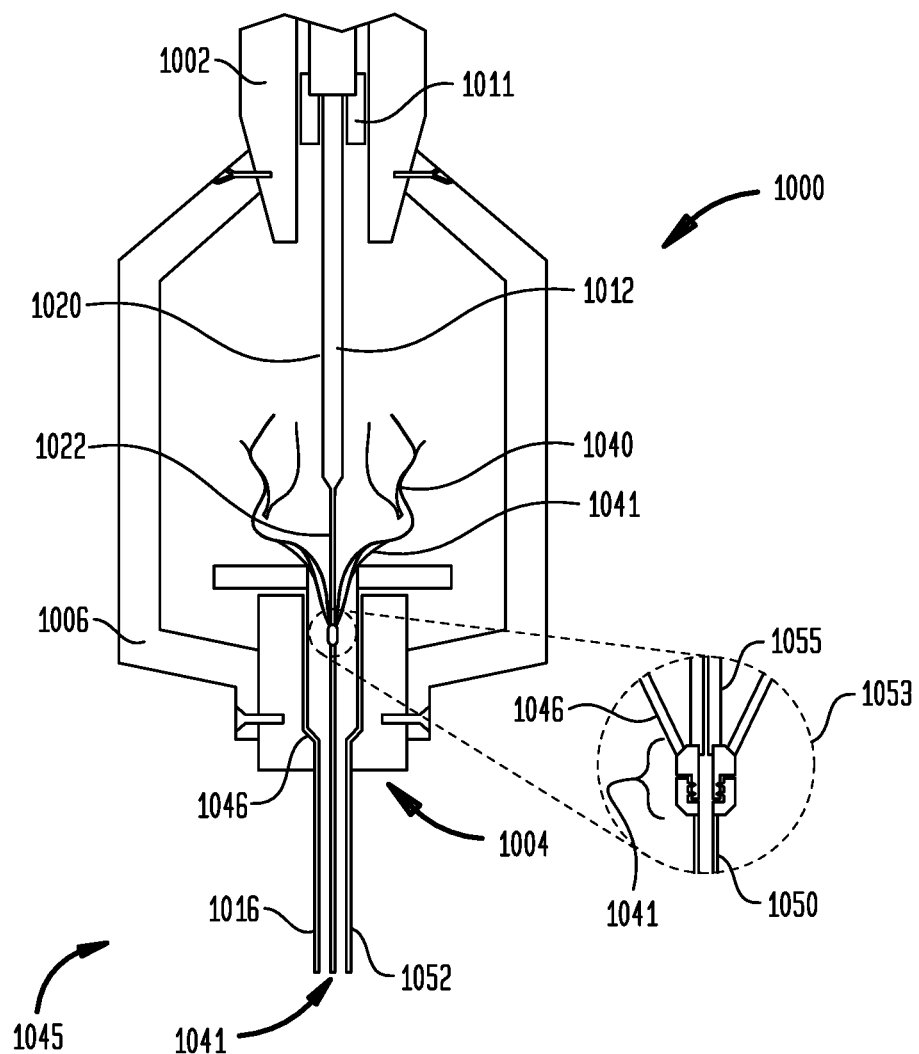
Figure 10D:
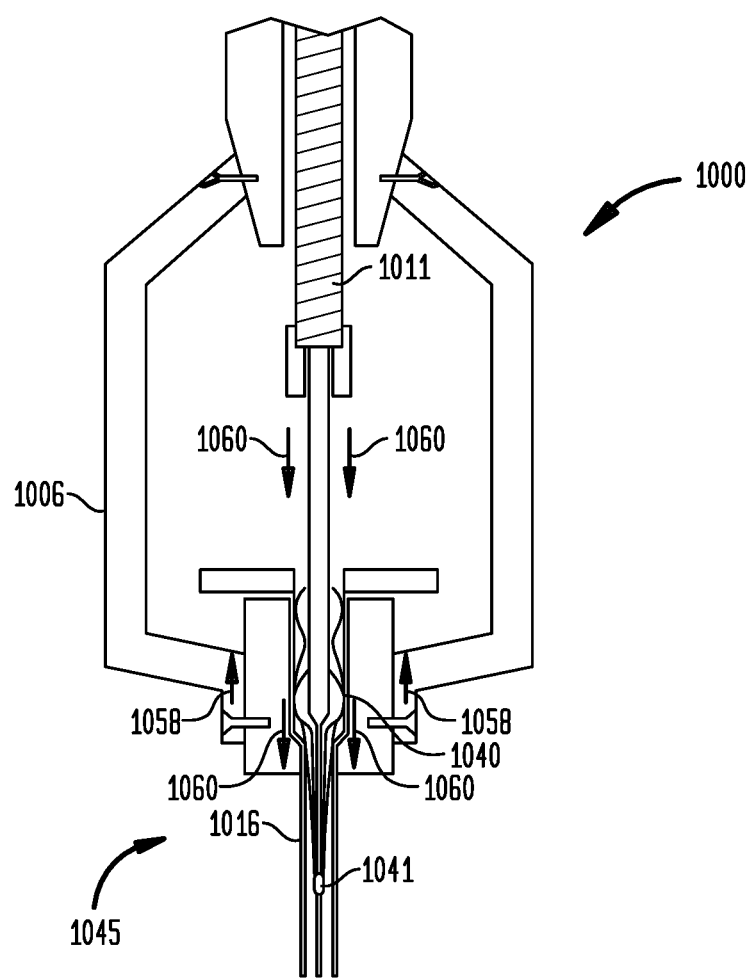
Figure 10E:
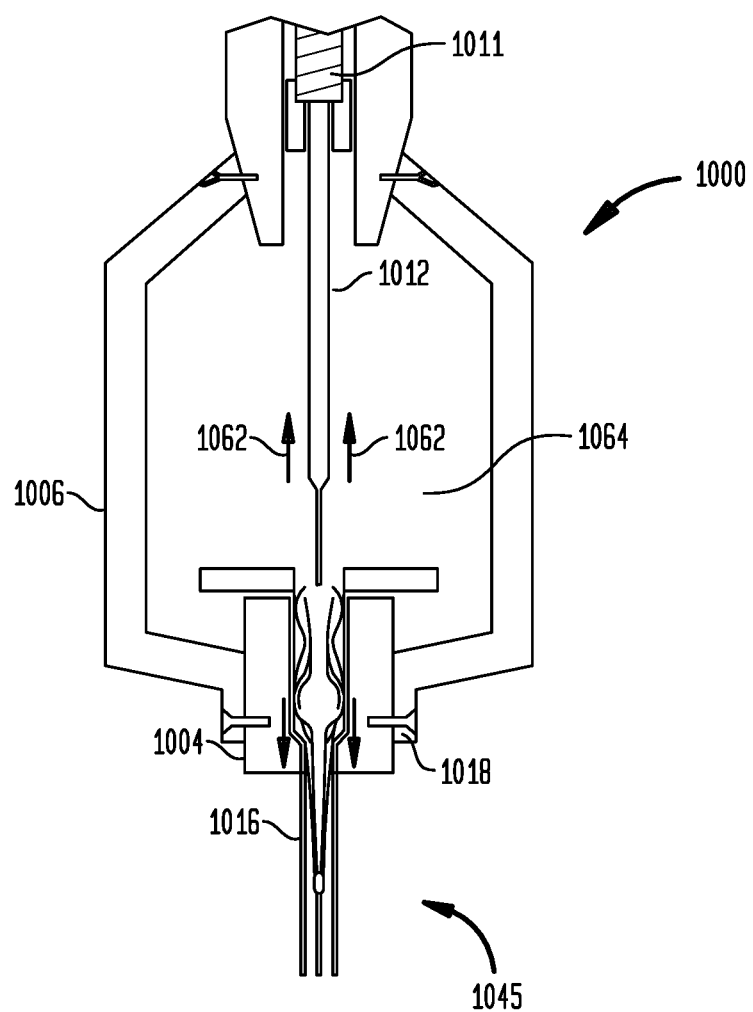

FIGS. 10C-10E show section views of the loading device 1000 being used to load a valve into a delivery system 1045, according to some embodiments. FIG. 10C shows loading device 1000 during a pre-packing process. The valve retention mechanism 1041 of a valve 1040 can be coupled to an inner catheter 1050. Close up view 1053 shows a threaded connection between the retention mechanism 1041 and the inner catheter 1050, according to some embodiments. The retention mechanism 1041 can include or be coupled to one or more sutures 1046 (e.g., sutures, tabs, tethers, loops). In some embodiments, the walls of the delivery catheter 1016 includes one or more internal layers to accommodate valves of different sizes and shapes, as needed. In some cases, the delivery catheter 1016 includes one or more outer layers 1052 (also referred to as outer sheaths). The brace 1004 of the loading device 1000 can have an opening that fits over an outer diameter of the delivery catheter 1016. In some cases, an opening of the brace 1004 has a larger diameter portion 1046 that accommodates a shoulder portion of the delivery catheter 1016.

When the knob 1008 of the loading tool 1000 is turned, the packing rod 1012 can place a pushing force upon the inner catheter 1050 at a load transfer area 1055, thereby causing the valve 1040 to be pulled into and collapse within the delivery catheter 1016. The inner catheter 1050 can facilitate guiding of the valve 1040 such that the valve is centered within the delivery catheter 1016. The inner catheter 1050 may prevent (or reduce the occurrence of) the valve 1040 from twisting during the loading. The packing rod 1012 can be tapered such that the distal portion 1022 applies a concentrated pushing force in a central region of the load transfer area 1055 to facilitate symmetric collapse of the valve 1040. The larger diameter proximal portion 1020 can maintain a central position of the valve 1040 as the proximal portion 1020 enters the delivery catheter 1016, thereby facilitating symmetric collapse of the valve 1040.

FIG. 10D shows the valve 1040 in a further progressively packed state within the delivery catheter 1040. Bracing arms 1006 can secure the position of the loading device 1000 with respect to the delivery catheter 1016, thereby providing a negative resistance 1058 to the forward force 1060 of the advancing packing rod 1012 during the loading operation. If readjustments of the position of the valve 1040 are needed, the packing rod 1012 can be retracted and re-advanced into the delivery catheter 1040 until the valve 1040 is sufficiently packed. Once the valve 1040 is determined to be adequately packed, the packing rod 1012 can be decoupled from the valve retention mechanism 1041.

FIG. 10E shows a post-packing operation, whereby the threaded rod 1011 is turned (e.g., by the knob 1008) to move the packing rod 1012 a reverse 1062 direction, thereby retracting the packing rod 1012 from within the delivery catheter 1016 and leaving the collapsed valve 1040, with the valve retention mechanism 1041, in the delivery catheter 1016. Once the packing rod 1012 is sufficiently retracted, the loading device can be decoupled from the delivery catheter 1016 by unfastening the fasteners 1018 (e.g., screws) to remove one or more of the bracing arms 1006 and brace 1004. In some embodiments, the removal involves sliding the delivery catheter 1016 radially out of the brace 1004. The delivery system 1045 is then loaded with valve 1040 for delivery into the patient.

In some embodiments, a balloon can be situated in a region 1064 internal to the bracing arms 1006 to provide further support for the packing rod 1012 during forward and/or reverse movement of the packing rod 1012. For example, the balloon can be inflated during forward movement 1060 (FIG. 10D) of the packing rod 1012 to provide lateral support for the packing rod 1012. The balloon can then be deflated prior to or during movement of the packing rod 1012 in the reverse 1062 direction in order to reduce forces on and/or interaction with the valve 1040 (e.g., valve leaflets).

Figure 11A:
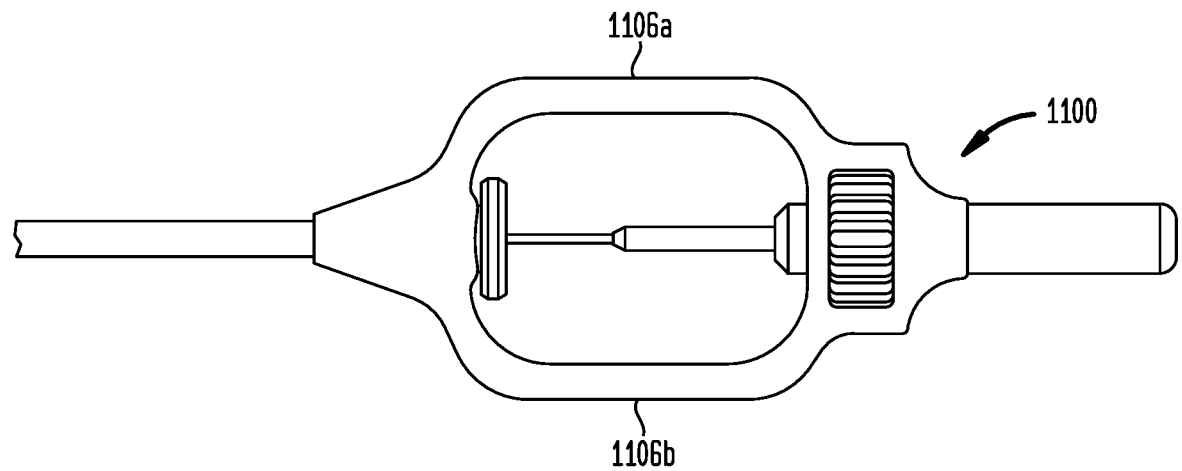
FIGS. 11A-11B show another exemplary loading device.
Figure 11B:
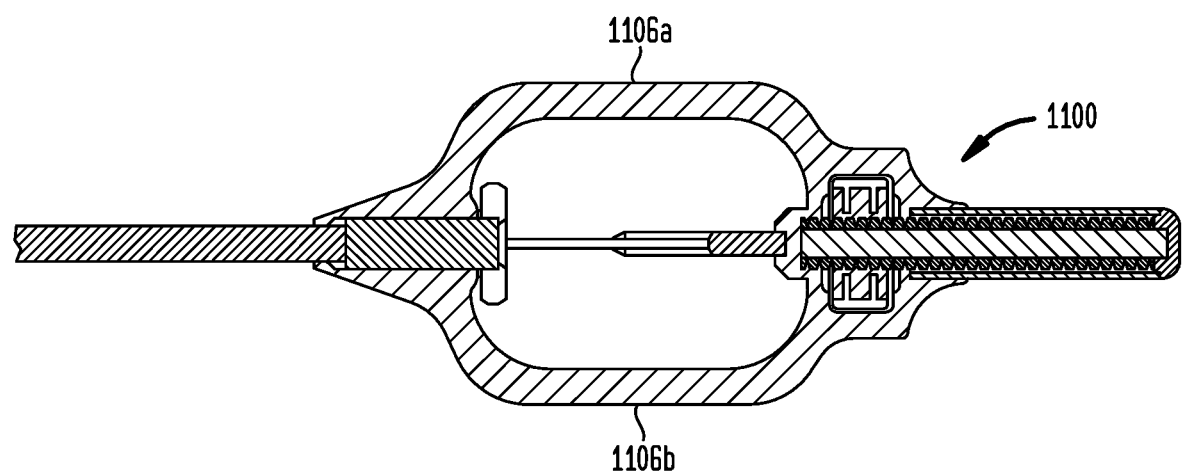

According to some embodiments, the direct loading device has two bracing arms. FIGS. 11A and 11B show a perspective view and section view, respectively, of a loading device 1100 having two bracing arms 1106. A two-arm configuration may provide different features than a three-arm configuration. For example, a two-arm configuration may provide better access to the valve positioned therein compared to a three-arm configuration. The two-arm configuration may be easier to maneuver during a loading operation (e.g., be less bulky). The two-arm configuration may be easier to manufacture and require less manufacturing material compared to a three-arm configuration. The three-arm configuration may provide better stability of the valve during the loading process compared to two-arm configuration.

Figure 12:
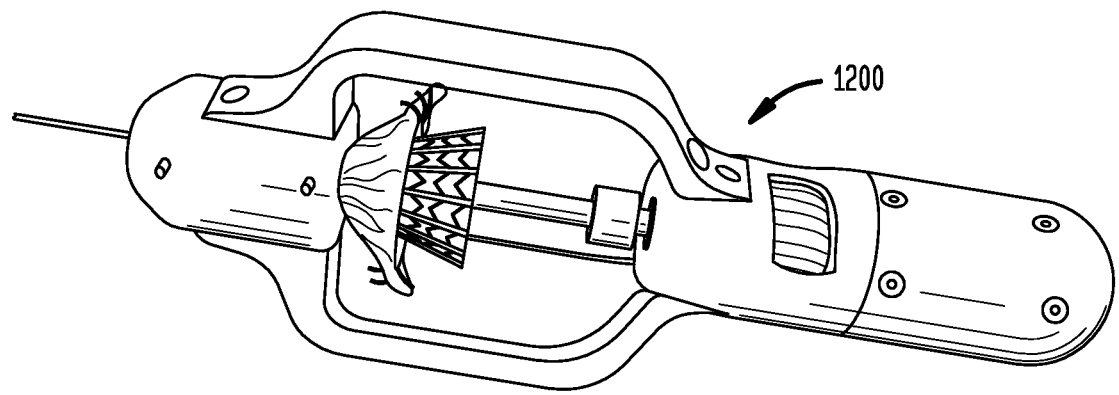
FIGS. 12 and 13 show exemplary valve holder assemblies and loading devices.
Figure 13:
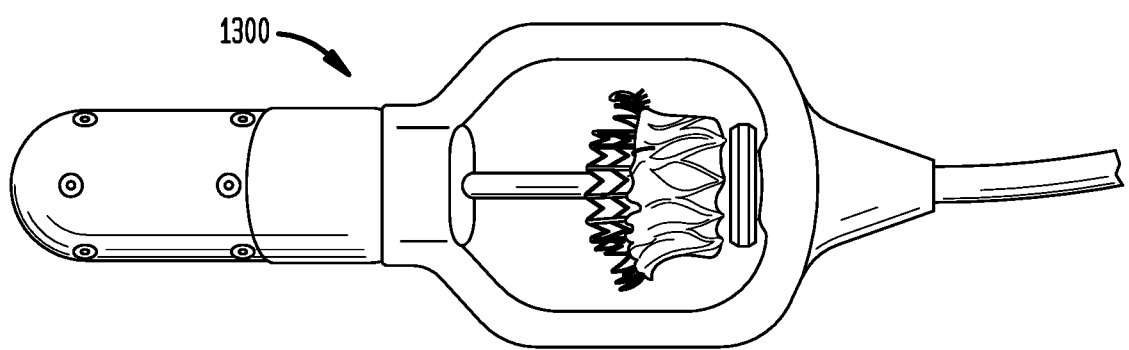

FIGS. 12 and 13 show a three-arm loading device 1200 and a two-arm loading device 1300, respectively, at various stages of loading valves into delivery catheters. In some cases, the three-arm loading device 1200 is configured to stably sit on a surface (e.g., table) during the loading process. In some cases, the two-arm loading device 1300 is configured to be supported by a user during the loading process.

The sizes and shapes of various components of the loading devices described herein can be configured to accommodate requirements of particular applications. For example, in some applications it may be beneficial to have a shorter or longer loading device. FIG. 14 show exemplary loading devices 1400 and 1420 have different lengths. A shorter loading device 1420 can reduce that distance that the valve travels during loading, thereby reducing the chances of corrosion of parts of the valve. In some cases, a shorter removable sheath 1422 is used to contain the valve (e.g., compared to a longer removable sheath 1420).

Any of the loading devices described herein can be configured to be exposed to an autoclaving process. For example, the material (e.g., polymer, silicone, metal and/or ceramic) of various parts of the loading device may be durable enough to withstand the high temperature and conditions of autoclaving. If polymer materials are used, the polymer components can be configured to withstand repeated heat cycling during autoclaving. In some embodiments, the polymer components are replaced with non-polymer components (e.g., metal and/or ceramic). In some cases, portions of the loading device may be configured to shrink to minimize possible corrosion of the valve enclosed therein (e.g., when exposed to a solution).

Figure 15A:
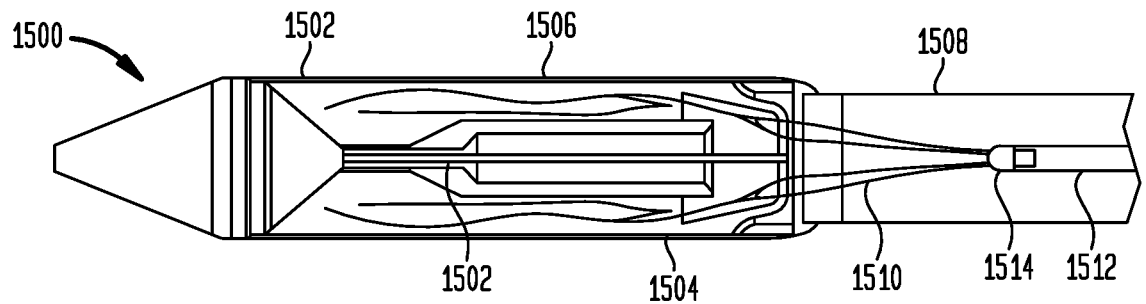
FIGS. 15A-15C show an exemplary delivery device with a leave-in mandrel.
Figure 15B:
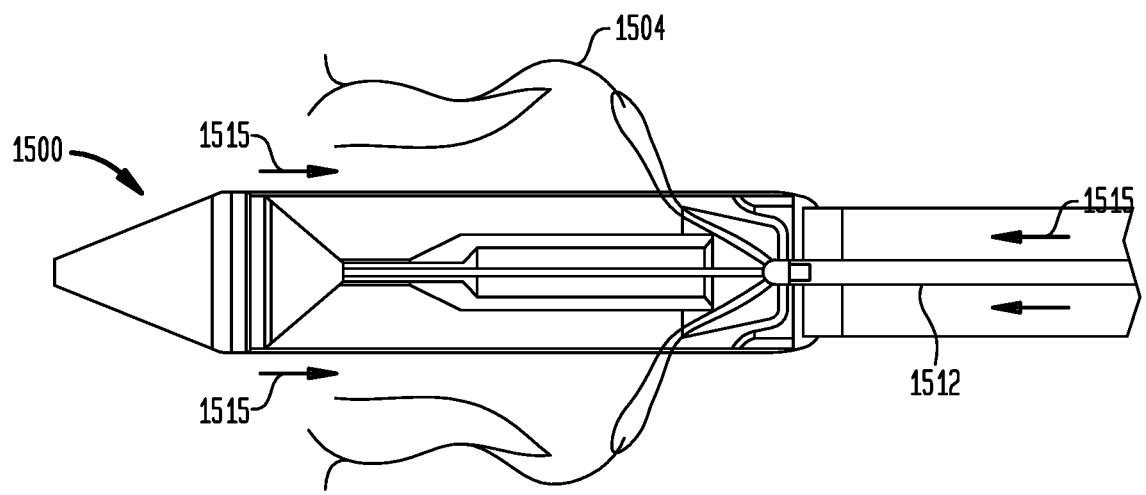
Figure 15C:
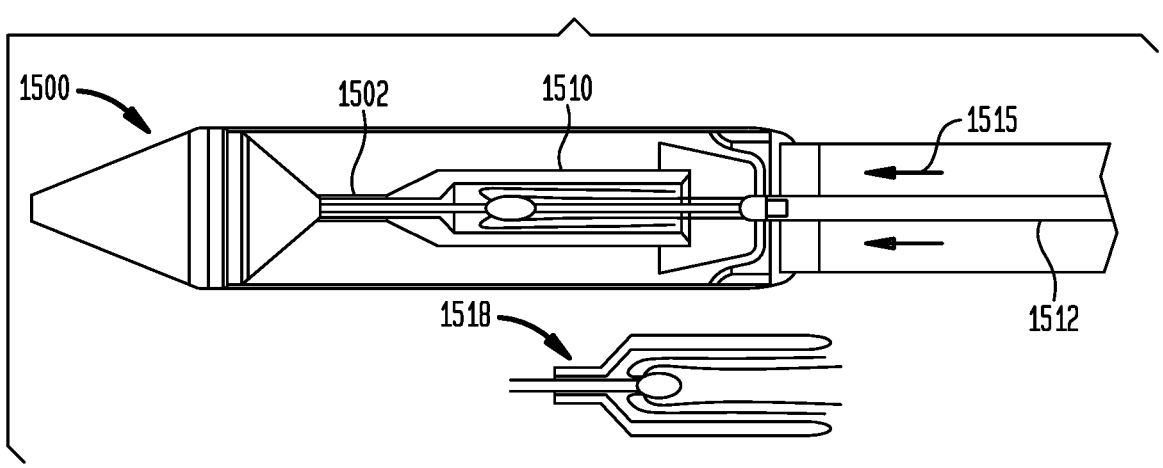

Any of the loading device described can be implemented with a leave-in mandrel. A leave-in mandrel refers to a mandrel that remains within the delivery system with the collapsed valve. Once the delivery system delivers the valve (without the leave-in mandrel) into the patient, the leave-in mandrel can remain within the delivery device. FIGS. 15A-15C show section views of an exemplary delivery system 1500 having a leave-in mandrel 1502. At FIG. 15A, the valve 1504 is loaded within the delivery catheter 1506 such that the collapsed valve 1504 is supported by the leave-in mandrel 1502. In preparation for delivering into the patient, a suture catheter 1512 can be coupled to a suture ring 1514, which is in turn coupled to sutures 1510. At 15B, the delivery catheter 1506 is pulled back in a backward direction 1515, and the suture catheter 1512 is extended in a forward direction 1516. This causes the petals of the valve 1504 to expand. After the valve 1504 has been deployed from the delivery catheter 1506, at FIG. 15C, the suture catheter 1512 can be extended further in the forward direction 1516 to pull the sutures 1510 off of the valve petal features to constrain the sutures 1510 tucked back and contained within the inner diameter of the delivery catheter 1506, as shown in close up view 1518. This increased constraint may ease the final release of the valve 1504, and/or may increase the ability to pull the sutures 1510 off in one motion regardless of coaxiality and/or centrality of delivery system relative to the valve 1510. The leave-in mandrel can keep the sutures 1510 constrained and avoid the sutures 1510 from catching during the valve delivery process. In some embodiments, the leave-in mandrel has a tapered end and open central region, which can minimize compression and prevent blocking of the sutures 1510.

Figure 16A:
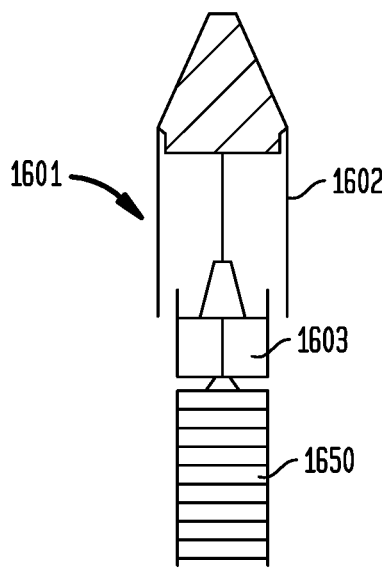
FIGS. 16A-16D show an exemplary process for using a chaser tube.
Figure 16B:
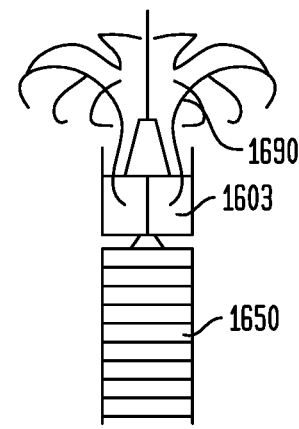
Figure 16C:
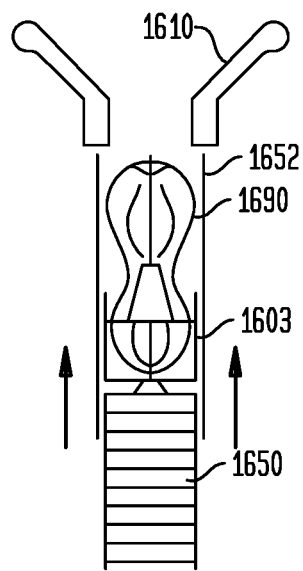
Figure 16D:
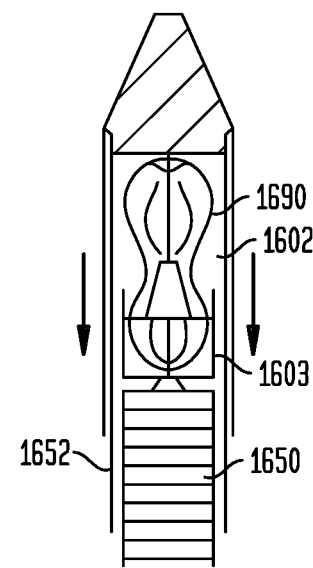

In some embodiments, a chaser tube can be used to directly load a valve into a split sheath delivery system. FIG. 16A shows a section view of a portion of an exemplary split sheath delivery system 1601 having a distal assembly 1650, a proximal sheath 1603 and a distal sheath 1602. FIGS. 16B-16D show how a chaser tube 1652 can be used the split sheath delivery system 1601. At FIG. 16B, the valve 1690 can first be loaded into the proximal sheath 1603 (e.g., via attachment of the proximal loops to the distal assembly 1650) such that at least the proximal anchor is collapsed therein. The chaser tube 1652 is positioned around the distal assembly 1650 in a proximal direction. At FIG. 16C, the chaser tube 1652 is pulled distally over the proximal sheath 1603 to collapse the distal anchor and load the valve 1690 therein. In this embodiment, the diameter of the chaser tube 1652 is greater than the diameter of a proximal sheath 1603 (and can be, for example, substantially equal to the diameter of a distal sheath 1602). In some embodiments, a loading cone 1610 is optionally used to guide the collapsing of the ventricular petals of the valve 1690. Once loaded inside the chaser tube 1652, at FIG. 16D, the distal sheath 1602 can be pulled proximally thereover as the chaser tube 1603 is pulled proximally. The chaser tube 1603 can then be removed (e.g., cut, unclamped, or otherwise removed). The chaser tube 1603 can advantageously be used with embodiments of a split sheath delivery system where a retaining mechanism is not detachable from the rest of a distal assembly of the delivery device. Examples of split sheath delivery systems are described in International Patent Application No. PCT/US2017/062045 and U.S. Provisional Application No. 62/621,692, each of which is incorporated herein in its entirety.

Although described as being used for the trans-septal delivery method, the delivery devices described herein can also be used for a trans-atrial or surgical delivery methods.

Aspects of the delivery devices and methods may be combined with aspects of the delivery devices and methods described in U.S. patent application Ser. No. 14/677,320, U.S. Pat. No. 8,870,948, or International Patent Application filed May 13, 2016 and titled "REPLACEMENT MITRAL VALVES," the entirety of which is incorporated by reference herein.

Although described herein for use with a mitral valve prosthetic, the delivery systems described herein can be used with a variety of different implantable devices, including stents or other valve prosthetics.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A loading device configured to radially collapse an expandable medical implant, the loading device comprising:
   an operating handle having an opening therein extending along a longitudinal axis thereof;
   a brace coupled to the operating handle and configured to interface with a distal end of a delivery system configured to deploy the expandable medical implant, the brace having a lumen extending therethrough in a direction parallel to the longitudinal axis;
   a plurality of brace arms that extend from the brace to the operating handle, the brace arms being configured to transfer a force acting on the brace along the longitudinal axis directly to the operating handle;
   a packing rod extending between the operating handle and the brace in first and second longitudinal directions parallel to the longitudinal axis; and
   a control element movable relative to the operating handle, movable relative to the packing rod and coupled to the packing rod, the control element being configured to translate the packing rod relative to the operating handle and the brace in the first and second longitudinal directions.

2. The loading device of claim 1, further comprising a threaded rod extending within the opening parallel to the longitudinal axis and affixed to the packing rod, wherein the control element is an actuation knob threadedly engaged with the threaded rod, such that rotational motion of the actuation knob causes the threaded rod and the packing rod to translate in one of the first or second longitudinal directions.

3. The loading device of claim 1, wherein the plurality of brace arms includes three brace arms that are circumferentially spaced apart from one another about the longitudinal axis, and one of the three brace arms is configured to be selectively uncoupled from the operating handle and the brace.

4. The loading device of claim 1, wherein the lumen of the brace defines a funnel having a first diameter at a proximal end of the brace and a second diameter at a distal end of the brace, the first diameter being greater than the second diameter.

5. The loading device of claim 4, wherein the brace has a flange at the proximal end of the brace, the flange having a proximal-facing surface extending in a plane oriented substantially perpendicular to the longitudinal axis, the flange having a through-opening that defines the first diameter at the proximal end of the brace.

6. The loading device of claim 1, wherein the packing rod has a first outer diameter at a proximal end of the packing rod within the opening of the operating handle and a second outer diameter at a distal end of the packing rod within the lumen of the brace, the first diameter being greater than the second diameter.

* * * * *